(12) United States Patent
Turkington et al.

(10) Patent No.: US 10,548,579 B2
(45) Date of Patent: Feb. 4, 2020

(54) LEFT ATRIAL APPENDAGE IMPLANT

(71) Applicant: CARDIAC PACEMAKERS, INC., St. Paul, MN (US)

(72) Inventors: Marie Turkington, Co. Mayo (IE); Patrick Connolly, Galway (IE); Martyn G. Folan, Galway (IE); Fergal Horgan, Co. Mayo (IE)

(73) Assignee: Cardiac Pacemakers, Inc., St. Paul, MN (US)

( * ) Notice: Subject to any disclaimer, the term of this patent is extended or adjusted under 35 U.S.C. 154(b) by 563 days.

(21) Appl. No.: 15/213,999

(22) Filed: Jul. 19, 2016

(65) Prior Publication Data
US 2017/0027552 A1    Feb. 2, 2017

Related U.S. Application Data

(60) Provisional application No. 62/198,436, filed on Jul. 29, 2015.

(51) Int. Cl.
*A61M 29/00* (2006.01)
*A61B 17/00* (2006.01)
(Continued)

(52) U.S. Cl.
CPC ...... *A61B 17/0057* (2013.01); *A61B 17/1214* (2013.01); *A61B 17/12122* (2013.01);
(Continued)

(58) Field of Classification Search
CPC .......... A61B 17/0057; A61B 17/12186; A61B 17/12177; A61B 17/1219;
(Continued)

(56) References Cited

U.S. PATENT DOCUMENTS 5,375,612 A   12/1994   Cottenceau et al.
6,652,555 B1  11/2003   VanTassel et al.
(Continued)

FOREIGN PATENT DOCUMENTS

EP   2074953 A1   7/2009
WO   0027292 A1   5/2000
(Continued)

OTHER PUBLICATIONS

Romero et al., "Left Atrial Appendage Closure Devices," Clinical Medicine Insights: Cardiology, vol. 8, pp. 45-52, 2014.
(Continued)

*Primary Examiner* — Amy R Weisberg
(74) *Attorney, Agent, or Firm* — Seager, Tufte & Wickhem LLP

(57) ABSTRACT

A medical implant for a left atrial appendage may include a central member having an anchor at a distal end and a plurality of legs joined together at a joint coupled to the central member. The plurality of legs may be configured to expand from a delivery configuration to a deployed configuration. A medical implant may include a central shaft having an anchor at a distal end and a cup-shaped occluder fixed to a proximal end of the central shaft, the occluder being configured to expand from a delivery configuration to a deployed configuration and retard tissue ingrowth thereon. A medical implant system may include a delivery sheath, an implant having an expandable frame including a plurality of legs each having an anchor and a mesh having a plurality of openings therethrough attached to the frame, and a plurality of particles disposed within the delivery sheath.

4 Claims, 22 Drawing Sheets

(51) Int. Cl.
*A61B 17/12* (2006.01)
*A61F 2/01* (2006.01)

(52) U.S. Cl.
CPC .... *A61F 2/013* (2013.01); *A61B 2017/00588* (2013.01); *A61B 2017/00597* (2013.01); *A61B 2017/00623* (2013.01); *A61B 2017/00628* (2013.01); *A61B 2017/00632* (2013.01)

(58) Field of Classification Search
CPC ........ A61B 17/12172; A61B 17/12122; A61B 17/1214; A61B 2017/12054; A61B 2017/00588; A61B 2017/00623; A61B 2017/00628; A61B 2017/00632; A61B 2017/00597; A61F 2/013
See application file for complete search history.

(56) References Cited

U.S. PATENT DOCUMENTS

| | | | |
|---|---|---|---|
| 6,652,556 B1 * | 11/2003 | VanTassel | A61B 17/0057 606/200 |
| 6,689,150 B1 | 2/2004 | VanTassel et al. | |
| 6,958,061 B2 * | 10/2005 | Truckai | A61B 17/12022 606/213 |
| 6,994,092 B2 | 2/2006 | van der Burg et al. | |
| 7,128,073 B1 | 10/2006 | van der Burg et al. | |
| 7,972,359 B2 | 7/2011 | Kreidler | |
| 9,561,037 B2 * | 2/2017 | Fogarty | A61B 17/12022 |
| 9,561,097 B1 * | 2/2017 | Kim | A61B 17/12022 |
| 9,629,636 B2 * | 4/2017 | Fogarty | A61B 17/12022 |
| 10,071,181 B1 * | 9/2018 | Penegor | A61L 24/104 |
| 2003/0023266 A1 | 1/2003 | Borillo et al. | |
| 2003/0181942 A1 | 9/2003 | Sutton et al. | |
| 2004/0093012 A1 | 5/2004 | Cully et al. | |
| 2004/0158274 A1 | 8/2004 | WasDyke | |
| 2004/0215230 A1 | 10/2004 | Frazier et al. | |
| 2005/0015109 A1 * | 1/2005 | Lichtenstein | A61B 17/0057 606/200 |
| 2005/0070952 A1 | 3/2005 | Devellian | |
| 2005/0113861 A1 | 5/2005 | Corcoran et al. | |
| 2005/0288704 A1 | 12/2005 | Cartier et al. | |
| 2006/0015136 A1 * | 1/2006 | Besselink | A61F 2/013 606/200 |
| 2006/0030877 A1 | 2/2006 | Martinez et al. | |
| 2006/0100658 A1 * | 5/2006 | Obana | A61F 2/013 606/200 |
| 2006/0155323 A1 | 7/2006 | Porter et al. | |
| 2007/0066993 A1 | 3/2007 | Kreidler | |
| 2007/0083230 A1 | 4/2007 | Javois | |
| 2007/0150041 A1 * | 6/2007 | Evans | A61B 17/12118 623/1.11 |
| 2007/0162048 A1 | 7/2007 | Quinn et al. | |
| 2008/0275536 A1 * | 11/2008 | Zarins | A61F 2/07 623/1.11 |
| 2009/0105747 A1 | 4/2009 | Chanduszko et al. | |
| 2009/0112249 A1 * | 4/2009 | Miles | A61B 17/12122 606/192 |
| 2009/0318948 A1 * | 12/2009 | Linder | A61B 17/12022 606/191 |
| 2010/0004726 A1 * | 1/2010 | Hancock | A61B 17/12022 623/1.2 |
| 2010/0106178 A1 * | 4/2010 | Obermiller | A61B 17/0057 606/194 |
| 2011/0054515 A1 | 3/2011 | Bridgeman et al. | |
| 2011/0082495 A1 | 4/2011 | Ruiz et al. | |
| 2011/0301630 A1 * | 12/2011 | Hendriksen | A61B 17/12031 606/191 |
| 2012/0239083 A1 | 9/2012 | Kreidler | |
| 2013/0018413 A1 * | 1/2013 | Oral | A61B 5/0031 606/213 |
| 2015/0005810 A1 | 1/2015 | Center et al. | |
| 2015/0313605 A1 * | 11/2015 | Griffin | A61B 90/39 606/200 |

FOREIGN PATENT DOCUMENTS

| | | |
|---|---|---|
| WO | 2004012629 A1 | 2/2004 |
| WO | 2014018907 A1 | 1/2014 |

OTHER PUBLICATIONS

Invitation to Pay Additional Fees and, Where Applicable, Protest Fee, dated Oct. 13, 2016.

* cited by examiner

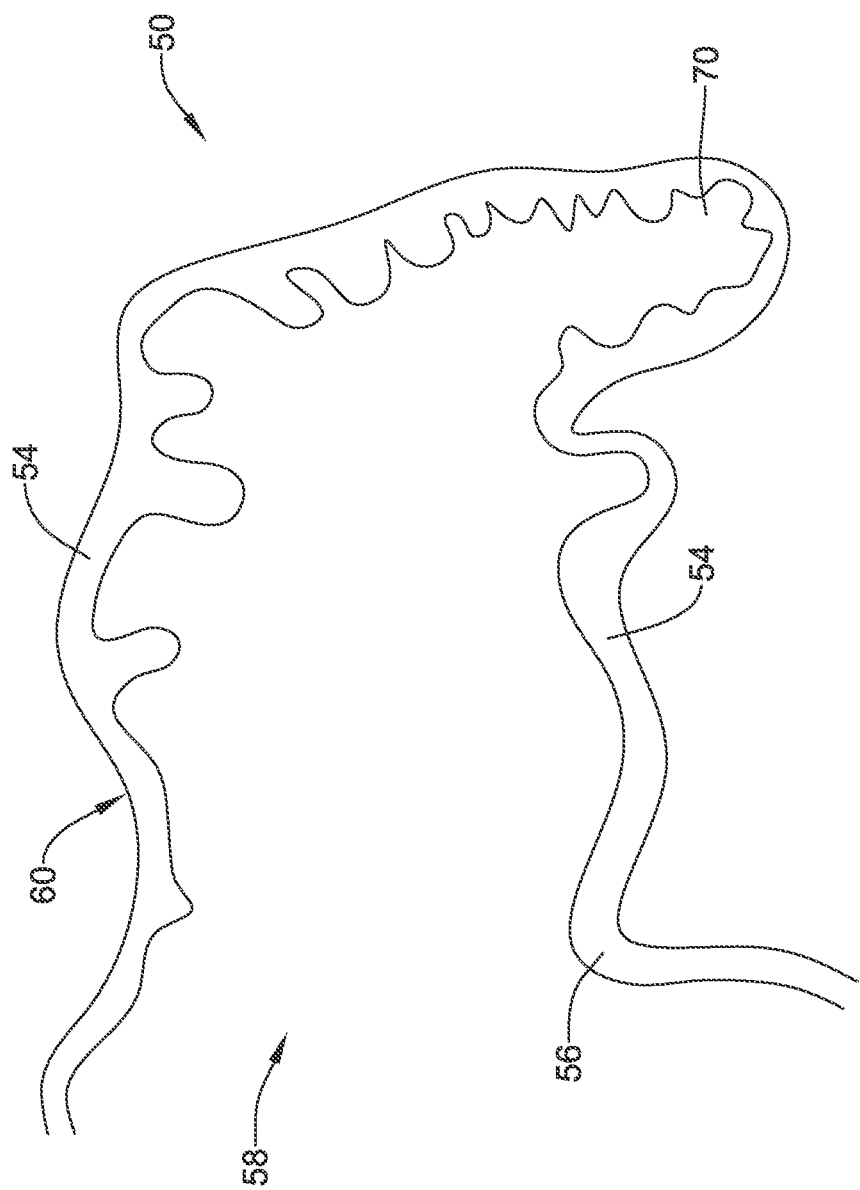

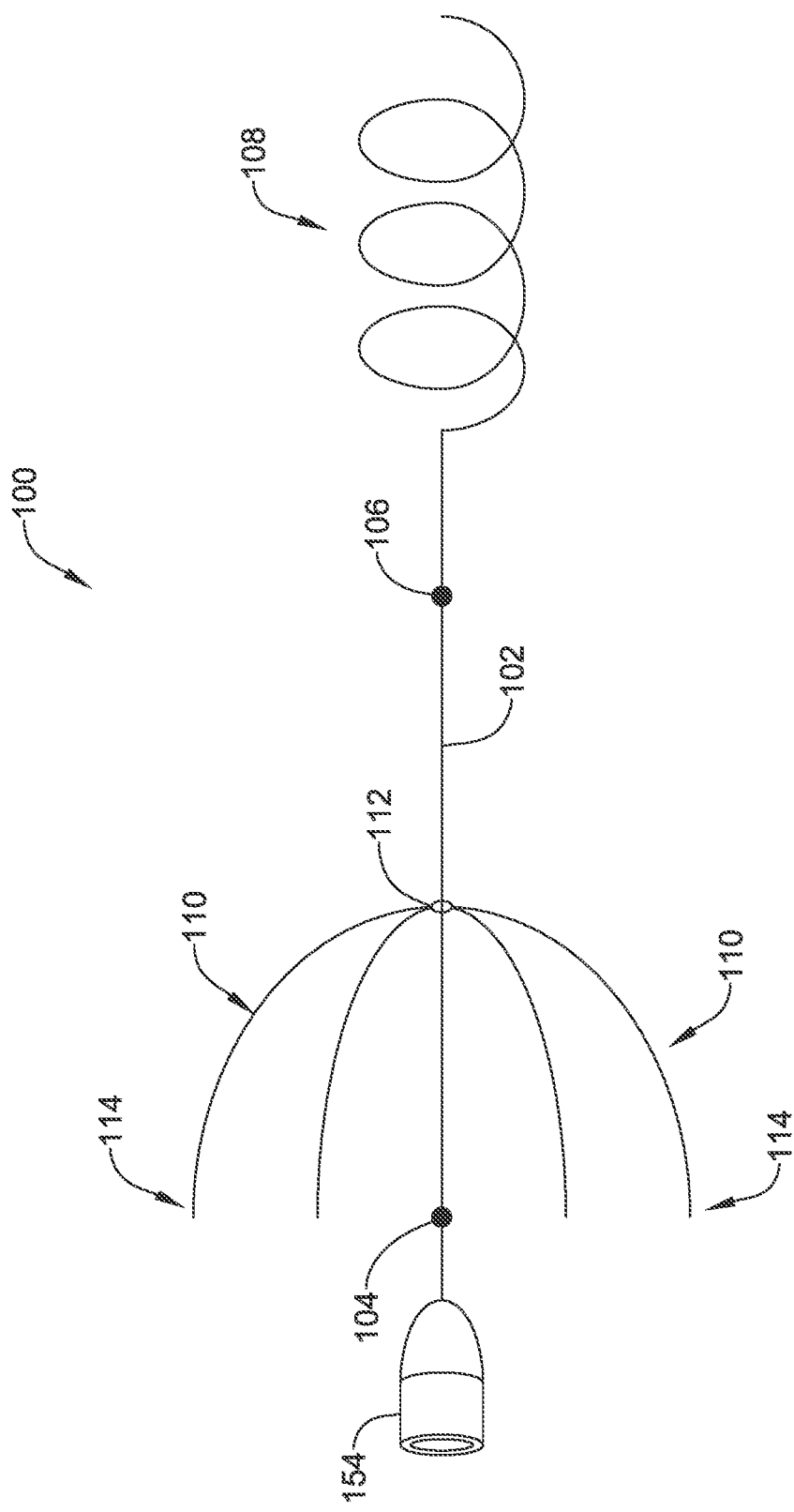

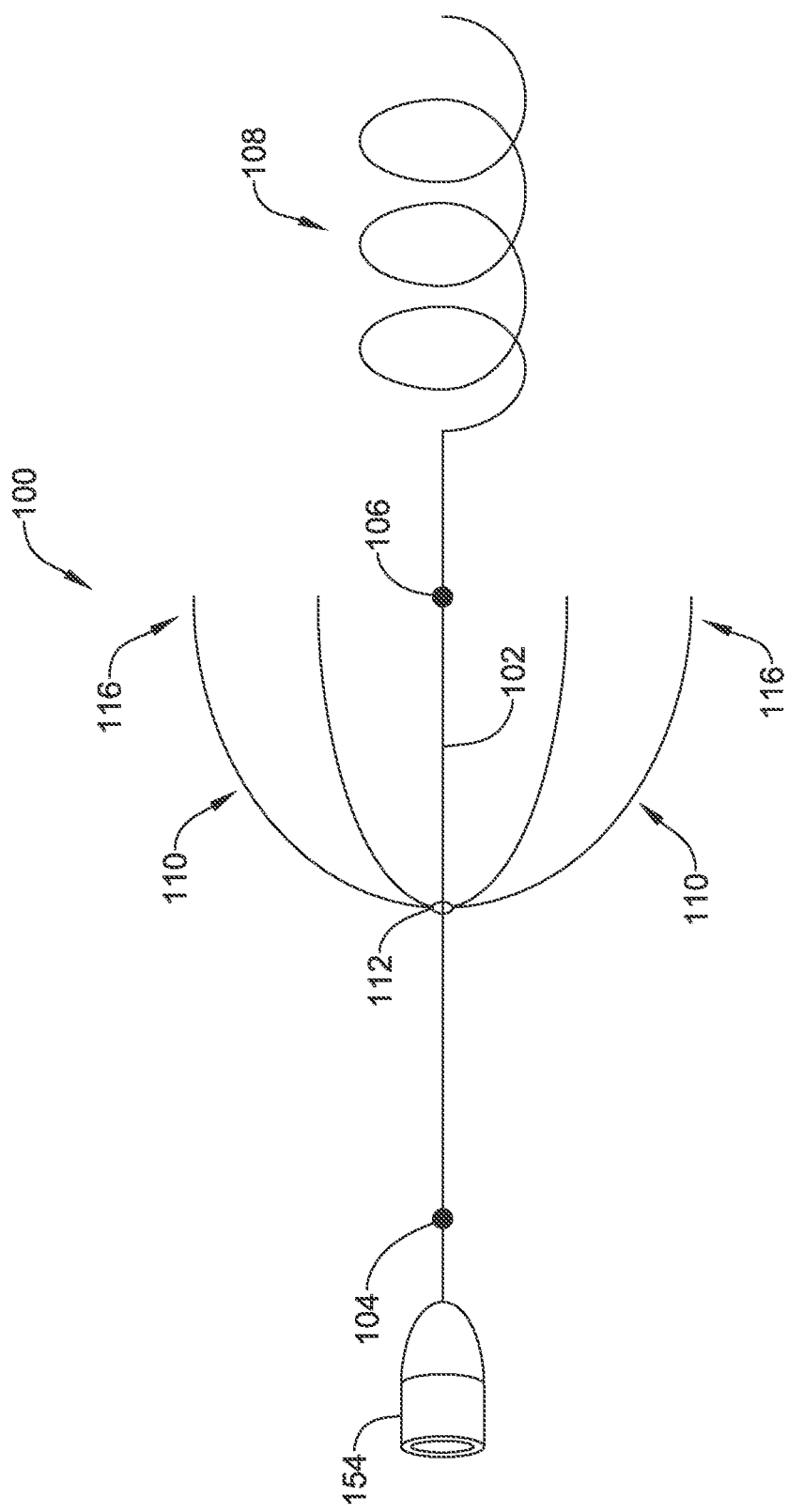

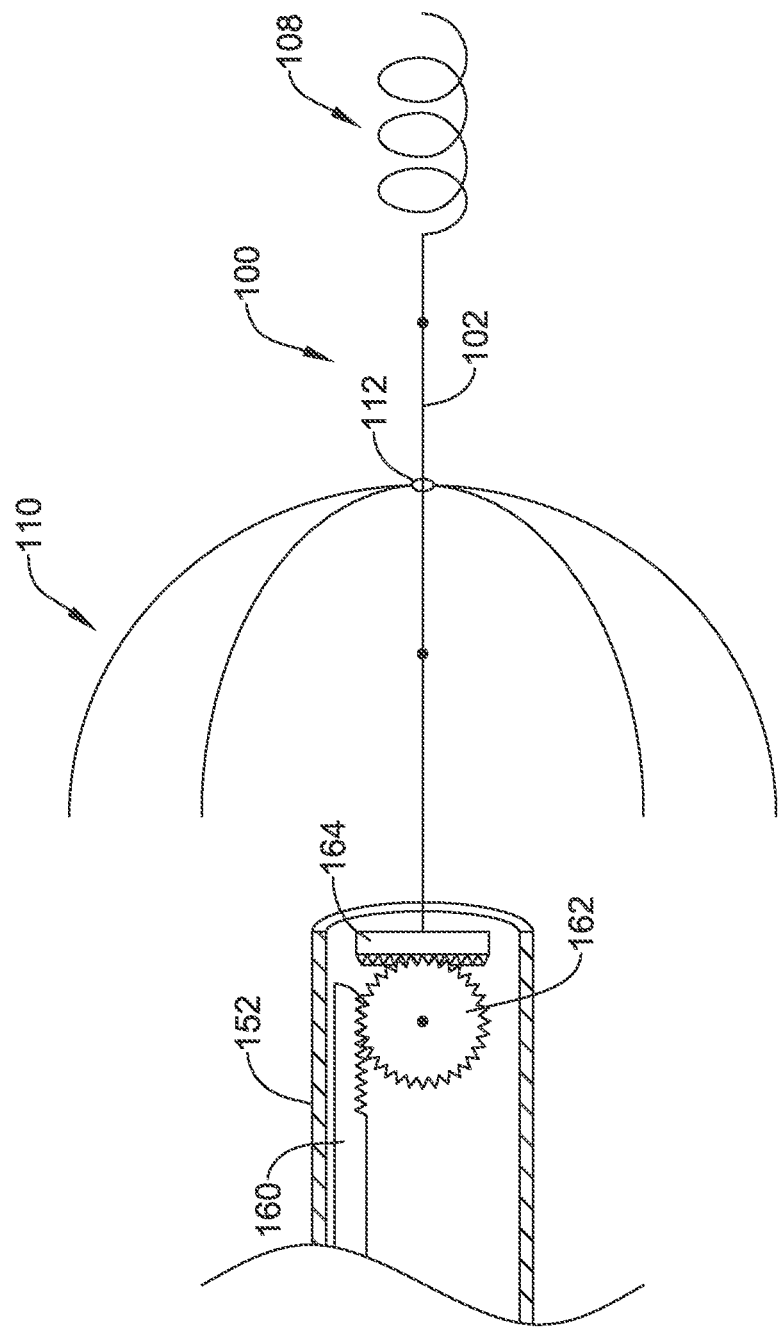

ium, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation originate in the left atrial appendage. As a treatment, medical devices have been developed which are deployed to close off the ostium of the left atrial appendage. Over time, exposed surface(s) of an implant spanning the ostium of the left atrial appendage may become covered with tissue (a process called endothelization), effectively removing the left atrial appendage from the circulatory system and reducing or eliminating the amount of thrombi which may enter the blood stream from the left atrial appendage.

Unfortunately, the left atrial appendage provides certain positive effects and/or functions, and closing the left atrial appendage off may have some negative side-effects. For example, stretch receptors of the left atrial appendage play a role in mediating thirst in hypovolemia. Effectively eliminating these receptors by closing off the left atrial appendage may cause hypertension and/or may negatively impact systemic blood pressure. Additionally, the left atrial appendage is highly dynamic, and modulates the relationship between pressure and volume, functioning as a natural decompression chamber. Left atrial appendage clamping may lead to an increase in diastolic transmitral and pulmonary flow velocities, and to an increase in left atrial mean pressure and size. Further still, the left atrial appendage is an endocrine organ which releases atrial natriuretic peptide (ANP). Endothelial cells of the left atrial appendage are specialized in the production and release of natriuretic peptides. In healthy human hearts, atrial natriuretic peptide concentration may be several times higher in the left atrial appendage than in the rest of the atrial free wall and in the ventricles. A continuing need exists for improved medical devices and methods to control thrombus formation within the left atrial appendage of patients suffering from atrial fibrillation while accommodating and/or maintaining the positive functionality of the left atrial appendage.

SUMMARY

In a first aspect, a medical implant for use in a left atrial appendage may comprise a central elongated member having an anchor at a distal end thereof, and a plurality of elongated metallic legs joined together at a joint, the joint being coupled to the central elongated member. The plurality of elongated metallic legs may be configured to expand radially outward from a delivery configuration to a deployed configuration.

In addition or alternatively, and in a second aspect, each of the plurality of elongated metallic legs extends proximally from the joint to a proximal tip.

In addition or alternatively, and in a third aspect, each of the plurality of elongated metallic legs extends distally from the joint to a distal tip.

In addition or alternatively, and in a fourth aspect, the central elongated member is rotatable within the joint.

In addition or alternatively, and in a fifth aspect, the anchor is fixed to the central elongated member.

In addition or alternatively, and in a sixth aspect, the anchor is a helical coil.

In addition or alternatively, and in a seventh aspect, the anchor includes one or more barbs extending radially outward from the central elongated member.

In addition or alternatively, and in an eighth aspect, the medical implant may further include a distal stop disposed on the central elongated member proximal of the anchor.

In addition or alternatively, and in a ninth aspect, the joint is disposed proximally of the distal stop.

In addition or alternatively, and in a tenth aspect, the medical implant may further include a proximal stop disposed on the central elongated member proximal of the distal stop.

In addition or alternatively, and in an eleventh aspect, the joint is disposed between the proximal stop and the distal stop.

In addition or alternatively, and in a twelfth aspect, the joint is axially slidable along the central elongated member between the proximal stop and the distal stop.

In addition or alternatively, and in a thirteenth aspect, a medical implant for use in a left atrial appendage may comprise a central elongate shaft having an anchor at a distal end thereof, and a cup-shaped occluder fixed to a proximal end of the central elongate shaft, the occluder being configured to expand radially outward from a delivery configuration to a deployed configuration. The occluder may be configured to retard tissue ingrowth thereon.

In addition or alternatively, and in a fourteenth aspect, the occluder is concave in a proximal direction.

In addition or alternatively, and in a fifteenth aspect, the occluder has a smooth surface substantially devoid of apertures.

In addition or alternatively, and in a sixteenth aspect, a medical implant system for use in a left atrial appendage may comprise an elongate delivery sheath having at least one lumen extending therethrough, an implant disposed within and deployable from the delivery sheath, the implant having an expandable frame including a plurality of legs each having an anchor at a distal end thereof, and a mesh attached to the expandable frame, the mesh having a plurality of openings therethrough, and a plurality of biocompatible, non-biodegradable particles disposed within the delivery sheath, wherein each of the plurality of particles is greater in size than all of the plurality of openings.

In addition or alternatively, and in a seventeenth aspect, the mesh is configured to retard tissue ingrowth thereon.

In addition or alternatively, and in an eighteenth aspect, the plurality of openings is sized and configured to prevent emboli from passing therethrough while permitting blood flow therethrough.

In addition or alternatively, and in a nineteenth aspect, delivery sheath is configured to release the plurality of particles distally of the implant.

In addition or alternatively, and in a twentieth aspect, after deployment of the implant in the left atrial appendage and release of the plurality of particles distally of the implant, the plurality of particles is retained within the left atrial appendage by the mesh and the plurality of particles is free-floating and configured to randomly move within the left atrial appendage to lyse emboli that form therein.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

FIG. 2 is a schematic partial cross-sectional view of an example left atrial appendage;

FIG. 3 is a schematic view of an example medical implant;

FIG. 3A is a schematic view of an example medical implant;

FIG. 19 is a partial section view of an example deployment mechanism for an example medical implant.

Figure 1:
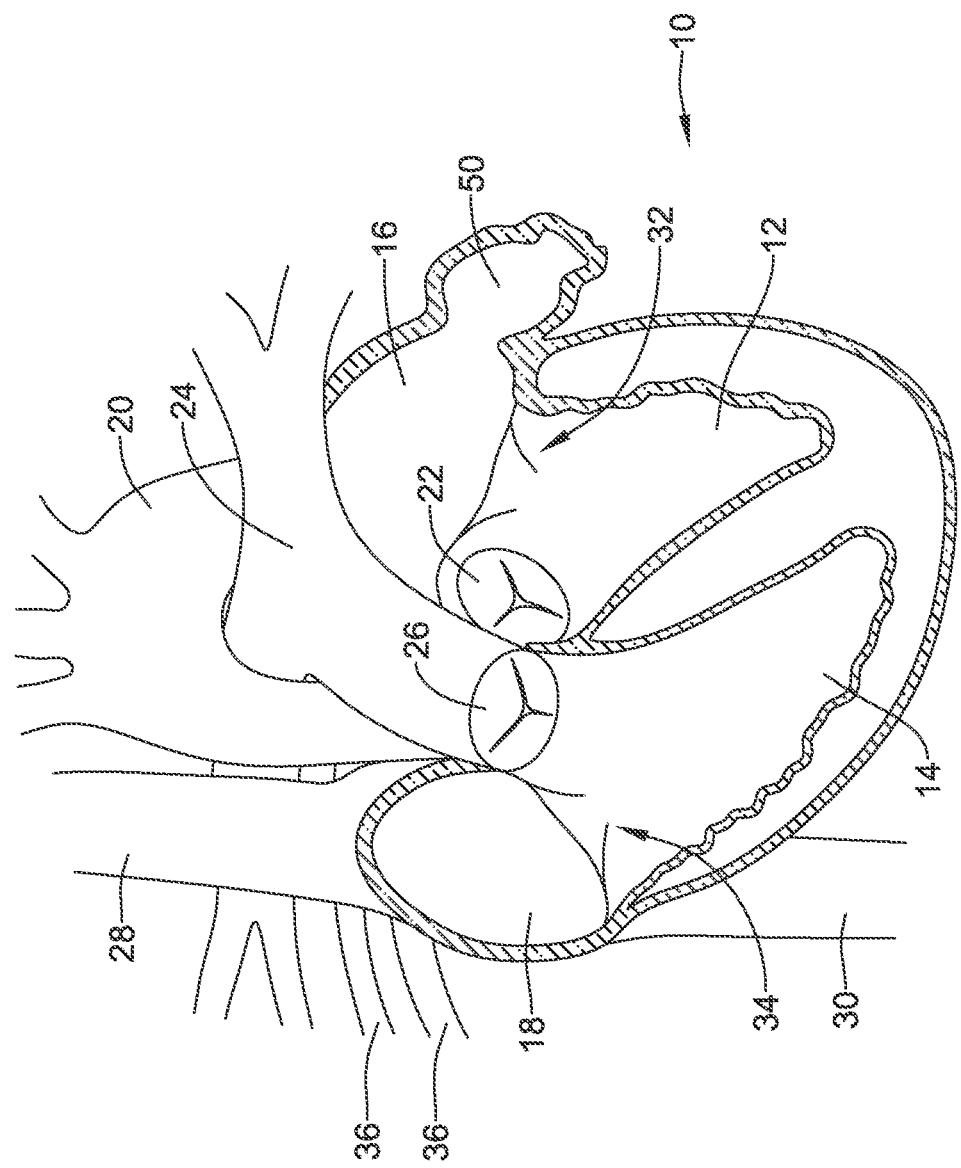
FIG. 1 is a schematic partial cross-sectional view of a heart.

While the invention is amenable to various modifications and alternative forms, specifics thereof have been shown by way of example in the drawings and will be described in greater detail below. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally be considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream" and "downstream" refer to a direction of fluid flow within a lumen, such as a body lumen or blood vessel.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage during atrial fibrillation may be due to stagnancy of the blood pool in the left atrial appendage. The blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. Further, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex with large irregular surface areas and a narrow ostium or opening compared to the depth of the left atrial appendage. These aspects as well as others, taken individually or in various combinations, may lead to high flow resistance of blood out of the left atrial appendage and/or formation of thrombi within the left atrial appendage.

In an effort to reduce the occurrence of thrombi formation within the left atrial appendage (and/or the release of thrombi from the left atrial appendage), to permit continued ANP production, and to maintain normal blood flow in and out of the left atrial appendage, among other benefits, medical devices have been developed that can be anchored in the left atrial appendage without closing the left atrial appendage completely off from the heart and/or circulatory system. As such, the suction effect of the left ventricle, either alone or in combination with contraction of the left atrium and/or left atrial appendage, may be sufficient to empty the left atrial appendage, prevent stagnant pooling of blood within the interior of the left atrial appendage, and/or to lyse any thrombi that do form. By reducing or eliminating the formation of thrombi, the risk of stroke due to thrombolytic material entering the blood stream from the left atrial appendage.

Similarly, or alternatively, in an effort to reduce the occurrence of thrombi formation within the left atrial appendage and maintain blood flow out of the left atrial appendage, a medical device has been developed that reduces the interior volume of the left atrial appendage without closing the left atrial appendage completely off from the heart and/or circulatory system. In reducing the volume of the interior of the left atrial appendage, less blood is present within the left atrial appendage. As such, the suction effect of the left ventricle, either alone or in combination with contraction of the left atrium and/or left atrial appendage, may be sufficient to empty the left atrial appendage and prevent stagnant pooling of blood within the interior of the left atrial appendage. By reducing or eliminating the stagnant pooling of blood, the formation of thrombi can be significantly reduced or avoided, thereby lowering the risk of stroke due to thrombolytic material entering the blood stream from the left atrial appendage. Additionally, ANP production and at least some normal blood flow into and out of the left atrial appendage may continue to occur.

Turning to the drawings, FIG. 1 is a partial cross-sectional view of certain elements of a human heart 10 and some immediately adjacent blood vessels. A heart 10 may include a left ventricle 12, a right ventricle 14, a left atrium 16, and a right atrium 18. An aortic valve 22 is disposed between the left ventricle 12 and an aorta 20. A pulmonary or semi-lunar valve 26 is disposed between the right ventricle 14 and a pulmonary artery 24. A superior vena cava 28 and an inferior vena cava 30 return blood from the body to the right atrium 18. A mitral valve 32 is disposed between the left atrium 16 and the left ventricle 12. A tricuspid valve 34 is disposed between the right atrium 18 and the right ventricle 14. Pulmonary veins 36 return blood from the lungs to the left atrium 16. A left atrial appendage 50 is attached to and in fluid communication with the left atrium 16.

FIG. 2 is a partial cross-sectional view of an example left atrial appendage 50. As discussed above, the left atrial appendage 50 may have a complex geometry and/or irregular surface area. Those skilled in the art will recognize that the illustrated left atrial appendage is merely one of many possible shapes and sizes for the left atrial appendage, which may vary from patient to patient. Those of skill in the art will also recognize that the medical devices and methods disclosed herein may be adapted for various sizes and shapes of the left atrial appendage, as necessary. A left atrial appendage 50 may include a generally longitudinal axis arranged along a depth of a main body 60 of the left atrial appendage 50. The main body 60 may include a wall 54 and an ostium 56 forming a proximal mouth 58. In some embodiments, a lateral extent of the ostium 56 and/or the wall 54 may be smaller or less than a depth of the main body 60 along the longitudinal axis, or a depth of the main body 60 may be greater than a lateral extent of the ostium 56 and/or the wall 54. In some embodiments, the left atrial appendage 50 may include a distalmost region 70, which may be formed or arranged as a tail-like element associated with a distal portion of the main body 60. In some embodiments, the distalmost region 70 may protrude radially or laterally away from the main body 60.

Figure 4:
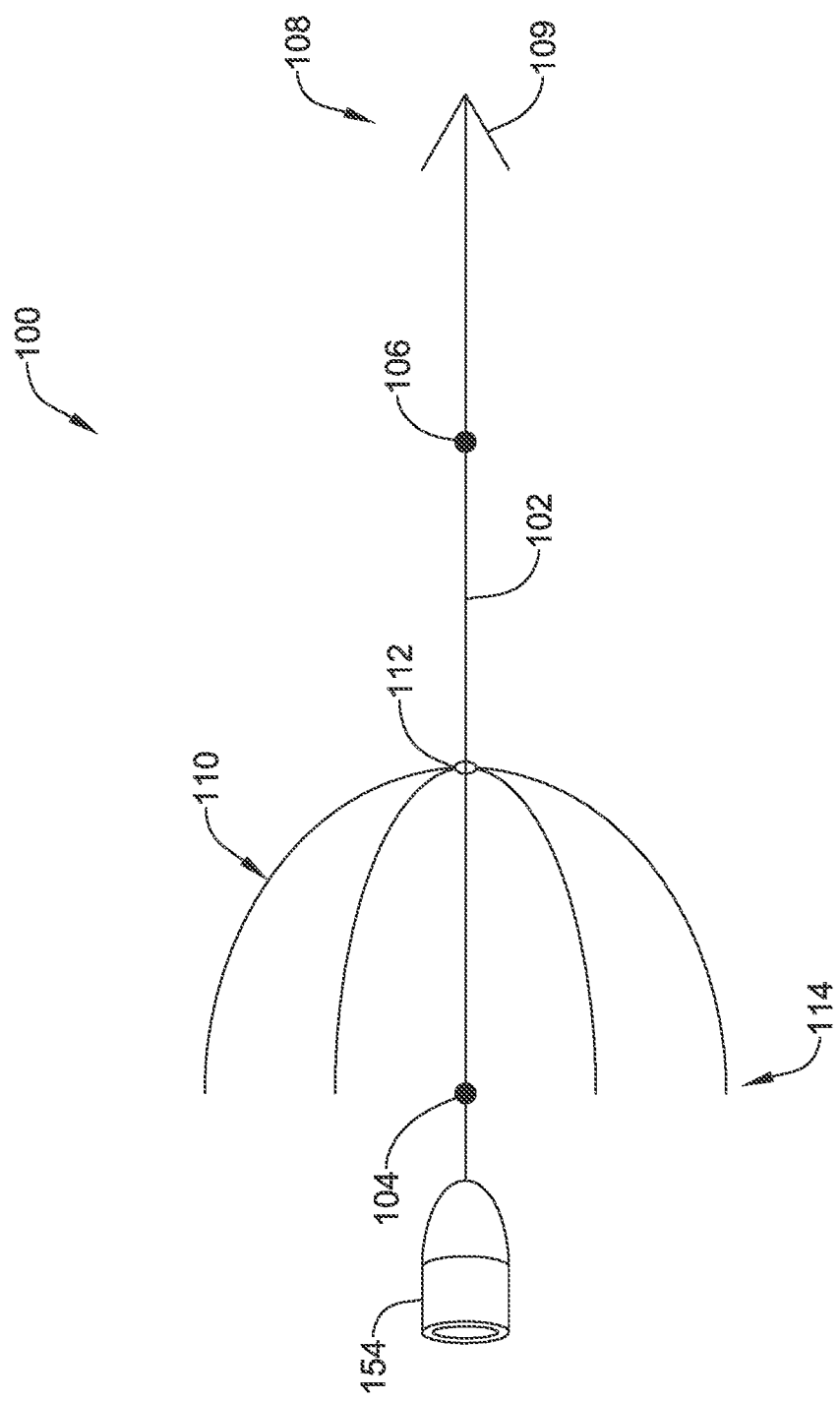
FIG. 4 is a schematic view of an example medical implant.

FIGS. 3 and 4 generally illustrate an example medical implant 100 for use in a left atrial appendage, the medical implant 100 including a central elongated member 102 having an attachment member 154 disposed at a proximal end and an anchor 108 disposed at a distal end thereof. In some embodiments, the anchor 108 may be fixed to and/or fixedly attached at the distal end of the central elongated member 102. In some embodiments, the medical implant 100 may include a plurality of elongated metallic legs 110 joined together at a joint 112. In at least some embodiments, the joint 112 may be coupled to and/or disposed about the central elongated member 102. In some embodiments, the joint 112 may be slidably coupled to the central elongated member 102, such that the joint 112 may be axially slidable along the central elongated member 102. In some embodiments, the joint 112 may be rotatably coupled to the central elongated member 102, such that the central elongated member 102 is rotatable within the joint 112. In some embodiments, the joint 112 may be both slidably coupled and rotatably coupled to the central elongated member 102, such that the central elongated member 102 is both slidable and rotatable within the joint 112.

In some embodiments, the medical implant 100 may include a distal stop 106 disposed on the central elongated member 102 proximal of the anchor 108 and/or distal of the attachment member 154. In some embodiments, the joint 112 may be disposed on and/or about the central elongated member 102 proximally of the distal stop 106. In some embodiments, the medical implant 100 may include a proximal stop 104 disposed on the central elongated member 102 distal of the attachment member 154. In some embodiments, the medical implant 100 may include the proximal stop 104 disposed on the central elongated member 102 proximal of the anchor 108 and/or proximal of the distal stop 106. In some embodiments, the joint 112 may be disposed on and/or about the central elongated member 102 distally of the proximal stop 104. In some embodiments, the joint 112 may be disposed on and/or about the central elongated member 102 between the proximal stop 104 and the distal stop 106, such that axial translation of the joint 112 along the central elongated member 102 is limited by the proximal stop 104 and the distal stop 106. In other words, the joint 112 may be axially slidable along and/or rotatable about the central elongated member 102 between the proximal stop 104 and the distal stop 106.

In some embodiments, the plurality of elongated metallic legs 110 may be configured to expand radially outward from a delivery configuration to a deployed configuration. In some embodiments, the plurality of elongated metallic legs 110 may be arranged and/or disposed generally parallel to the central elongated member 102 in the delivery configuration. In some embodiments, the plurality of elongated metallic legs 110 may be arranged and/or disposed extending radially outward from the central elongated member 102 in the deployed configuration. In some embodiments, the plurality of elongated metallic legs 110 may extend away from the central elongated member 102 at an oblique angle in the deployed configuration. In some embodiments, the plurality of elongated metallic legs 110 may extend away from the central elongated member 102 along a curve or a curvilinear arc. In some embodiments, the plurality of elongated metallic legs 110 may be self-biased toward the deployed configuration.

Figure 5:
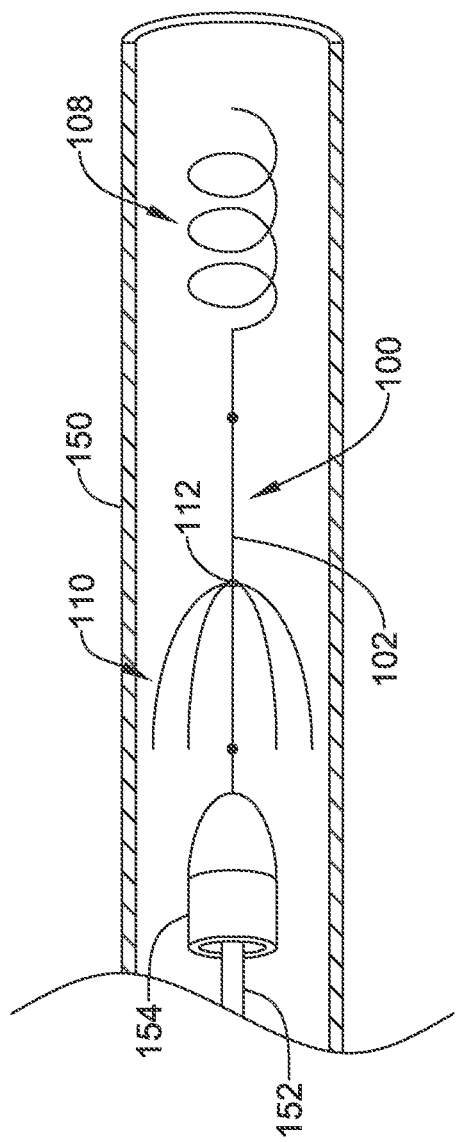
FIG. 5 is a partial schematic view of an example medical implant system.
Figure 6:
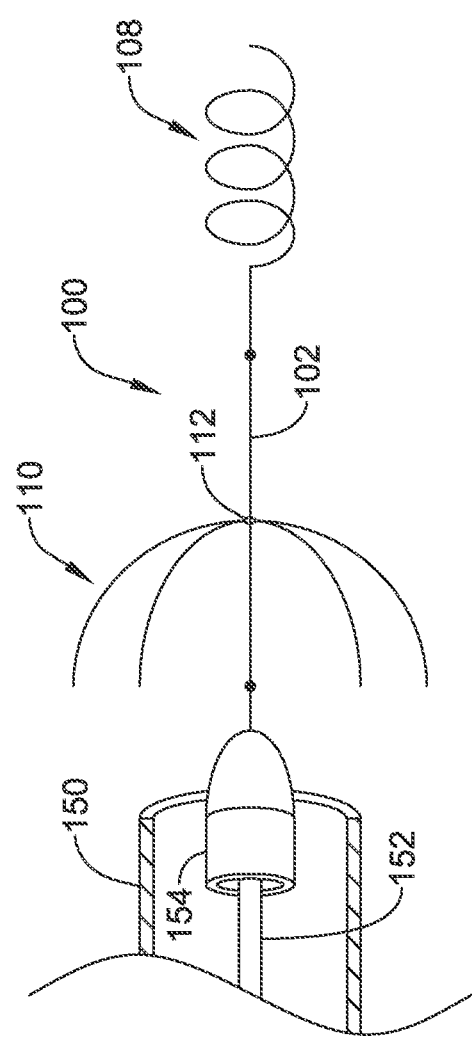
FIG. 6 is a partial schematic view of an example medical implant system.

In some embodiments, each of the plurality of elongated metallic legs 110 may extend proximally from the joint 112 to a proximal tip 114, as seen in FIGS. 3, 4, 5, 6, and, 7 for example. In at least some embodiments, the proximal tip(s) 114 may be disposed at an end of the elongated metallic legs 10 opposite the joint 112. In some embodiments, the plurality of elongated metallic legs 110 may be arranged and/or disposed extending proximally from the joint 112 to the proximal tip(s) 114 in the delivery configuration, as seen in FIG. 5, for example. In some embodiments, the plurality of elongated metallic legs 110 may be arranged and/or disposed extending proximally from the joint 112 to the proximal tip(s) 114 in the deployed configuration, as seen in FIG. 6 for example.

Figure 5A:
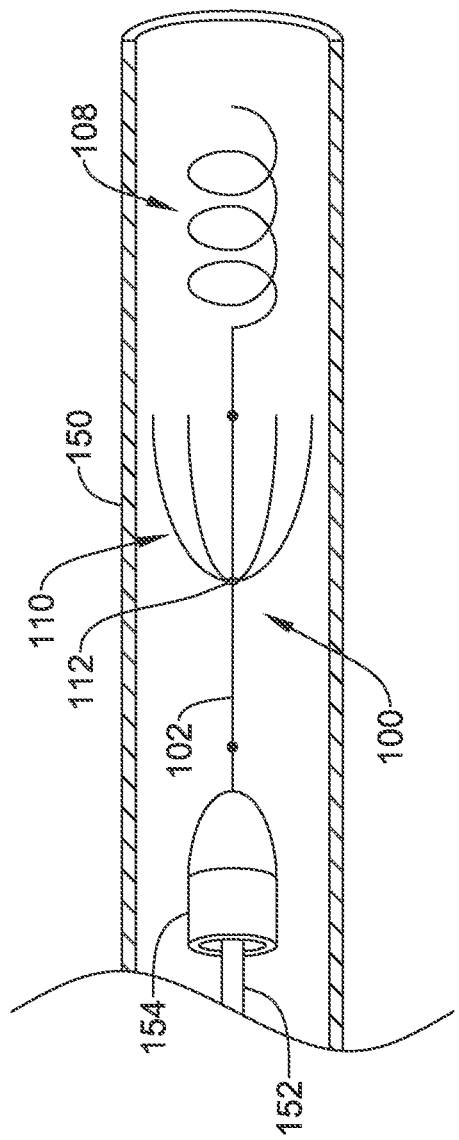
FIG. 5A is partial schematic view of an example medical implant system.
Figure 7:
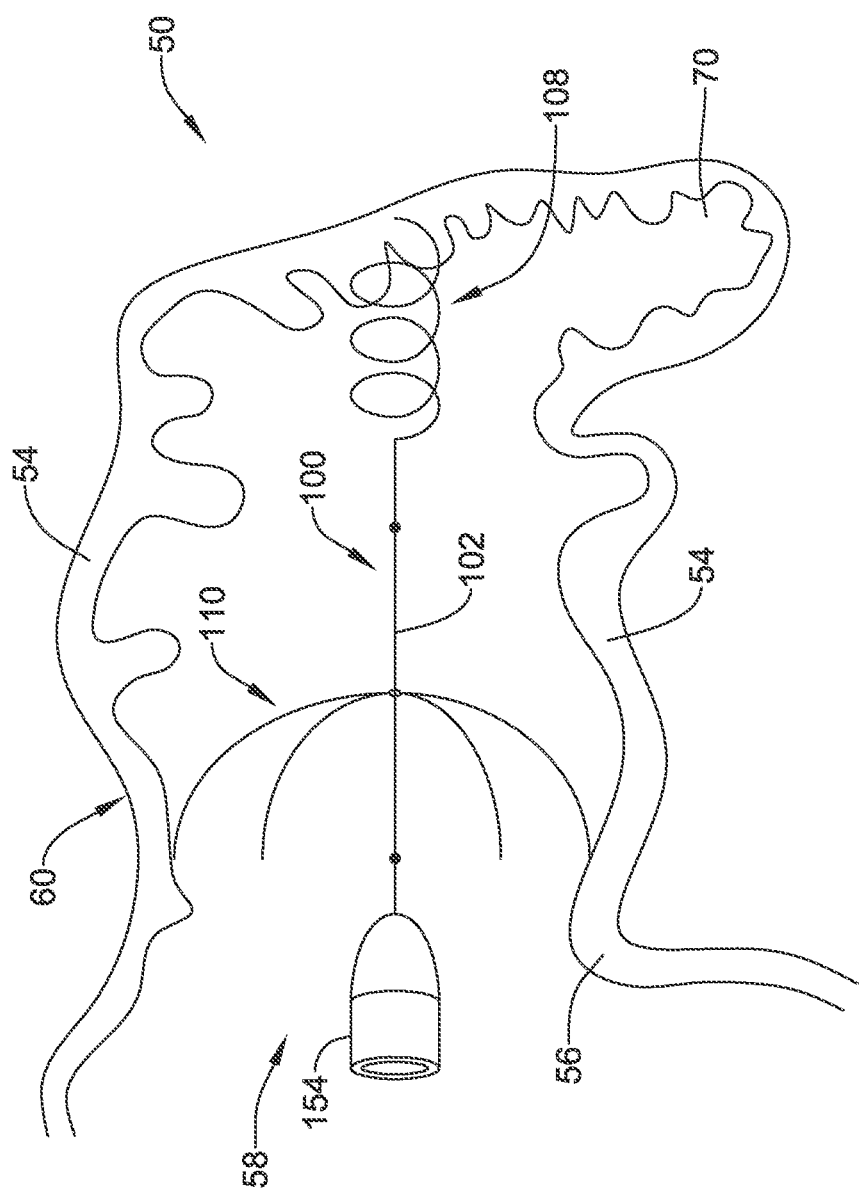
FIG. 7 is a partial schematic view of an example medical implant disposed within the example left atrial appendage of FIG. 2.
Figure 7A:
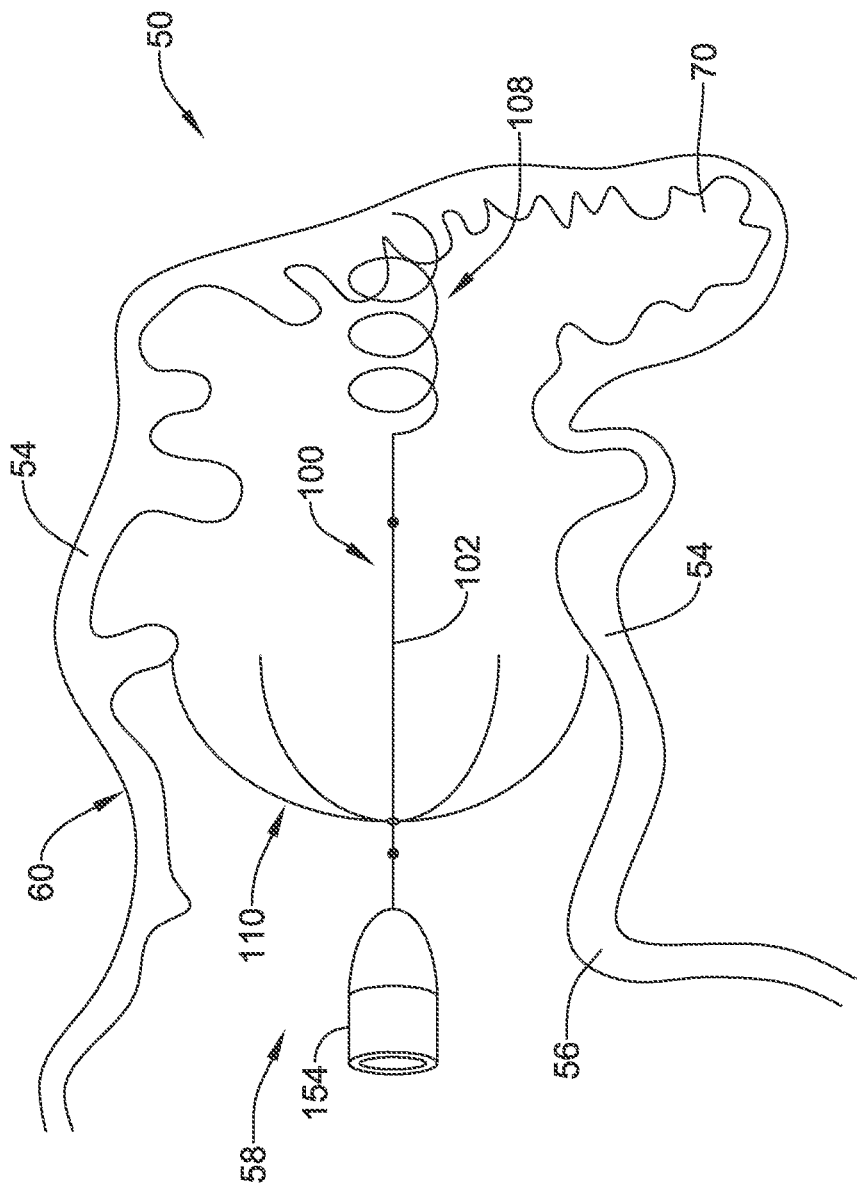
FIG. 7A is a partial schematic view of an example medical implant disposed within the example left atrial appendage of FIG. 2.

In some embodiments, each of the plurality of elongated metallic legs 110 may extend distally from the joint 112 to a distal tip 116, as seen in FIGS. 3A, 5A, and 7A for example. In at least some embodiments, the distal tip(s) 116 may be disposed opposite the joint 112 and/or toward the anchor 108. In some embodiments, the plurality of elongated metallic legs 110 may be arranged and/or disposed extending distally from the joint 112 to the distal tip(s) 116 in the delivery configuration. In some embodiments, the plurality of elongated metallic legs 110 may be arranged and/or disposed extending distally from the joint 112 to the distal tip(s) 116 in the deployed configuration.

In some embodiments, the medical implant 100 may include a central elongated member 102 having an anchor 108 disposed at, fixed to, and/or fixedly attached at a distal end thereof. In some embodiments, the anchor 108 may extend distally from the distal end of the central elongated member 102. In at least some embodiments, the anchor 108 may be configured to penetrate a wall 54 of a left atrial appendage 50. In some embodiments, the anchor 108 may be generally helical in shape or orientation, a helical structure including an inclined plane rotating continuously about a central axis of the anchor 108 (e.g., a screw or screw-like structure), and/or a helical coil, as seen in FIGS. 3 and 3A for example. In at least some embodiments, the anchor 108 may include a plurality of turns. In some embodiments, the anchor 108 may be formed from a polymeric or metallic material.

In some embodiments, the anchor 108 may include one or more barbs 109 extending radially outward from the central elongated member 102, as seen in FIG. 4 for example. In some embodiments, the one or more barbs 109 may be rigid and/or fixed in position relative to the central elongated member 102. In some embodiments, each of the one or more barbs 109 may extend proximally from the central elongated member 102 to a free end. In some embodiments, the one or more barbs 109 may be configured to actuate and/or shift between a retracted configuration (e.g., wherein the free end of each of the one or more barbs 109 may be positioned proximate the central elongated member 102) and a radially extended configuration (e.g., wherein the free end of each of the one or more barbs 109 may be positioned radially outward from the central elongated member 102 and/or the retracted configuration). In some embodiments, the one or more barbs 109 may be self-biased toward the radially extended position. In some embodiments, the one or more barbs 109 may include two barbs, three barbs, four barbs, five barbs, or more barbs as desired. In some embodiments, the one or more barbs 109 may be spaced equidistantly (e.g., at regular intervals or angles) about a central longitudinal axis of the central elongated member 102. In some embodiments, the one or more barbs 109 may be spaced irregularly about the central longitudinal axis of the central elongated member 102. In some embodiments, the one or more barbs 109 may be attached to the central elongated member 102 at a common axial position along the central elongated member 102. In some embodiments, the one or more barbs 109 may be positioned at a plurality of axial positions along the central elongated member 102.

As shown in FIGS. 5 and 5A, the medical implant 100 may be disposed within a lumen of a delivery sheath 150 in the delivery configuration, with the anchor 108 oriented distally. In at least some embodiments, a deployment shaft 152 may be disposed within the lumen of the delivery sheath 150 proximal of the medical implant 100. In some embodiments, the deployment shaft 152 may be releasably coupled to and/or engaged with an attachment member 154 disposed at a proximal end of the central elongated member 102 of the medical implant 100. In some embodiments, rotation of the deployment shaft 152 in a first direction (e.g., clockwise) may cause the central elongated member 102 and the anchor 108 fixed thereto to rotate in the first direction. The joint 112 may permit the central elongated member 102 to rotate relative to the plurality of elongated metallic legs 110.

The delivery sheath 150 and the medical implant 100, in the delivery configuration as seen in FIGS. 5 and 5A for example, may be advanced and/or navigated to a left atrial appendage (50, FIG. 2) or other suitable target site. In some embodiments, a distal end of the delivery sheath 150 may be advanced to the ostium (56, FIG. 2) of the left atrial appendage, but remain outside of the left atrial appendage itself. In some embodiments, a distal end of the delivery sheath 150 may be inserted past the ostium of the left atrial appendage and into the left atrial appendage. The deployment shaft 152 may be advanced distally within and/or relative to the delivery sheath 150 to advance and/or translate the anchor 108 out the distal end of the delivery sheath 150. In some embodiments, the deployment shaft 152 may be held stationary and the delivery sheath 150 may be retracted proximally relative to the deployment shaft 152 to advance and/or translate the anchor 108 out the distal end of the delivery sheath 150. After the anchor 108 is exposed at the distal end of the delivery sheath 150, the deployment shaft 152 may be advanced and/or rotated to insert the anchor 108 into the wall 54 of the left atrial appendage. In some embodiments, the anchor 108 may be inserted into the wall 54 while the plurality of elongated metallic legs 110 remains within the delivery sheath 150. In some embodiments, the plurality of elongated metallic legs 110 may be deployed from the delivery sheath 150 and/or disposed within the left atrial appendage before or while the deployment shaft 152 rotates the central elongated member 102 and/or the anchor 108.

A depth of deployment of the medical implant 100 within the left atrial appendage may be changed or modified in several ways. For example, since the plurality of elongated metallic legs 110 and/or the joint 112 is slidable along the central elongated member 102, an axial position of the joint 112 along the central elongated member 102 may be adjusted proximally or distally prior to deployment of the plurality of elongated metallic legs 110 from the delivery sheath 150, and to a slightly lesser degree, proximally or distally after deployment of the plurality of elongated metallic legs 110 from the delivery sheath 150, depending upon the orientation of the plurality of elongated metallic legs 110. Additionally, insertion depth of the anchor 108 into the wall of the left atrial appendage may also affect depth of deployment, as a deeper insertion depth of the anchor 108 may result in a deeper depth of deployment of the plurality of elongated metallic legs 110 and/or the joint 112. For example, in some embodiments, additional turns of rotation of the anchor 108 may bring the central elongated member 102 closer to the wall of the left atrial appendage and the medical implant 100 deeper into the left atrial appendage overall.

As shown in FIGS. 7 and 7A, after the anchor 108 has been inserted into the wall of the left atrial appendage, the delivery sheath 150 may be withdrawn proximally and removed from the patient, leaving the medical implant 100 disposed within the left atrial appendage, for example. In some embodiments, prior to withdrawing the delivery sheath 150, the deployment shaft 152 may be disengaged from and/or detached from the central elongated member 102.

Figure 15:
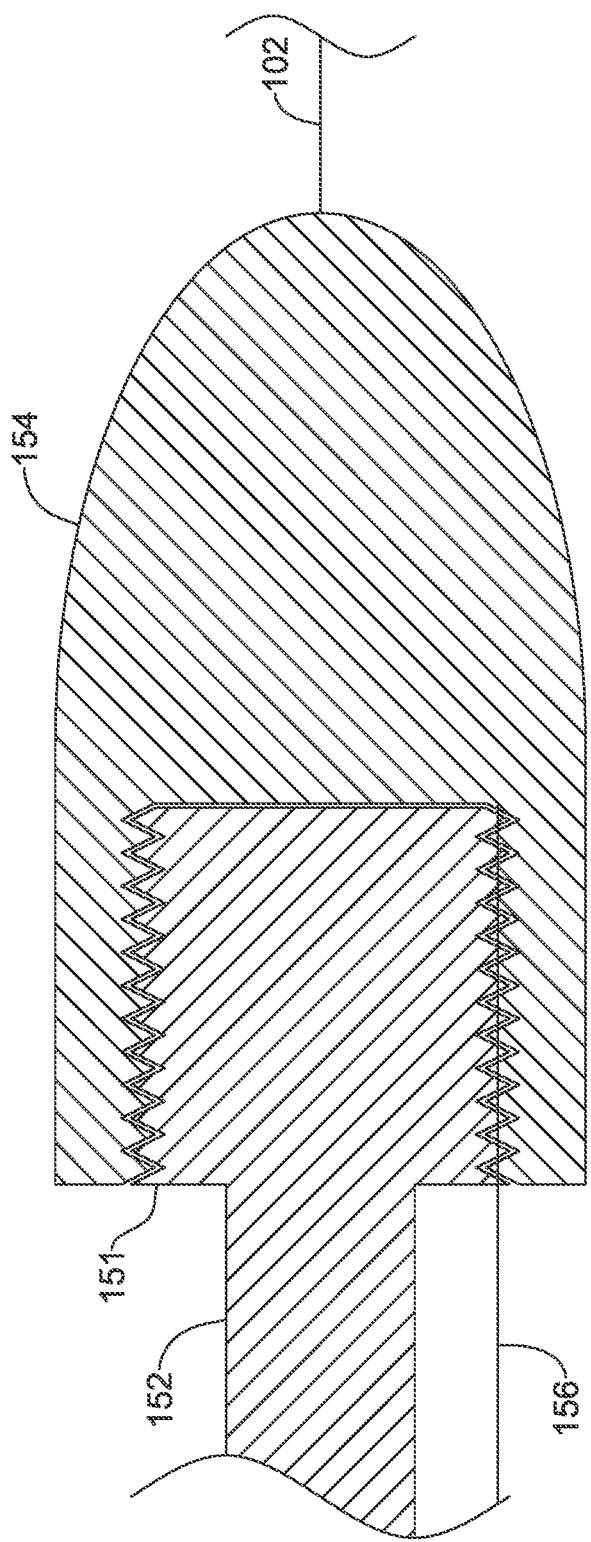
FIG. 15 is a partial section view of an example attachment member for an example medical implant.
Figure 16:
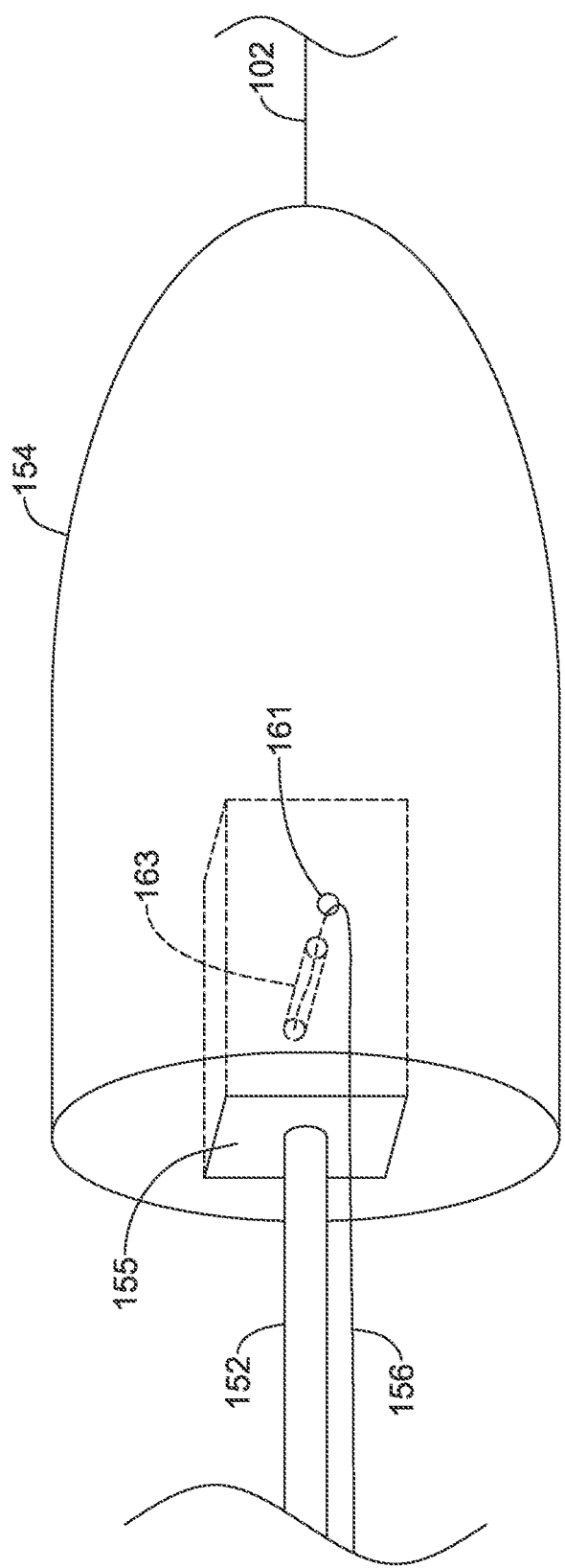
FIG. 16 illustrates an example attachment member for an example medical implant.

Some additional features and/or details about certain features that may be found in the medical implant 100 will be discussed further below. For example, in some embodiments, the deployment shaft 152 may include a male connector and the attachment member 154 may include a female connector configured to matingly receive the male connector therein and/or to engage with the male connector, as seen in FIGS. 15 and 16 and described in detail below. In some embodiments, the deployment shaft 152 may form or include a female connector and the attachment member 154 may form or include a male connector configured to engage with the female connector of the deployment shaft 152, as seen for example in FIGS. 17 and 18 and described in detail below.

Figure 8:
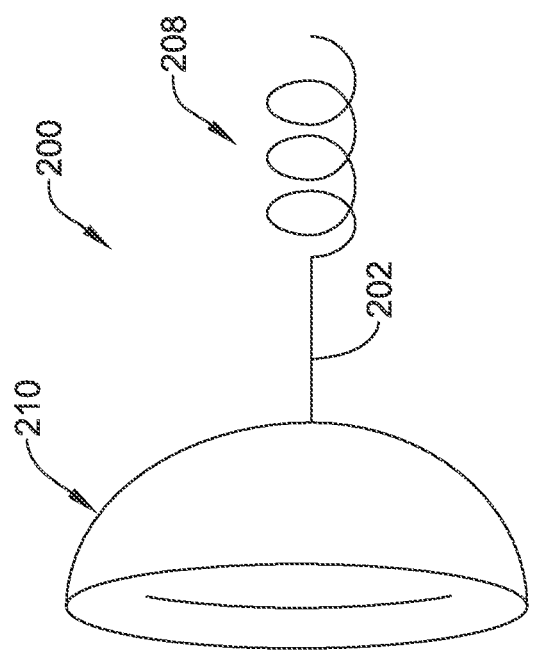
FIG. 8 is a schematic view of an example medical implant.

FIG. 8 generally illustrates an example medical implant 200 for use in a left atrial appendage (50, FIG. 2), the medical implant 200 including a central elongate shaft 202 having an anchor 208 disposed at a distal end thereof. In some embodiments, the anchor 208 may be fixed to and/or fixedly attached at the distal end of the central elongate shaft 202. In some embodiments, the medical implant 200 may include a cup-shaped occluder 210 fixed to a proximal end of the central elongate shaft 202. In some embodiments, the cup-shaped occluder 210 may include a polymeric membrane disposed on, over, and/or between an expandable support frame extending radially outward from the central elongate shaft 202. In some embodiments, the cup-shaped occluder 210 and/or the polymeric membrane may be configured to retard tissue ingrowth thereon. In some embodiments, the cup-shaped occluder 210 and/or the polymeric membrane may include an anti-thrombogenic surface, an anti-thrombogenic coating disposed thereon, an anti-thrombogenic agent embedded therein, and/or be made or formed from a non-thrombogenic polymer or polymeric composition. In some embodiments, the cup-shaped occluder 210 and/or the polymeric membrane may include or have a smooth surface substantially devoid of apertures, holes, openings, etc. extending through the polymeric membrane.

Figure 9:
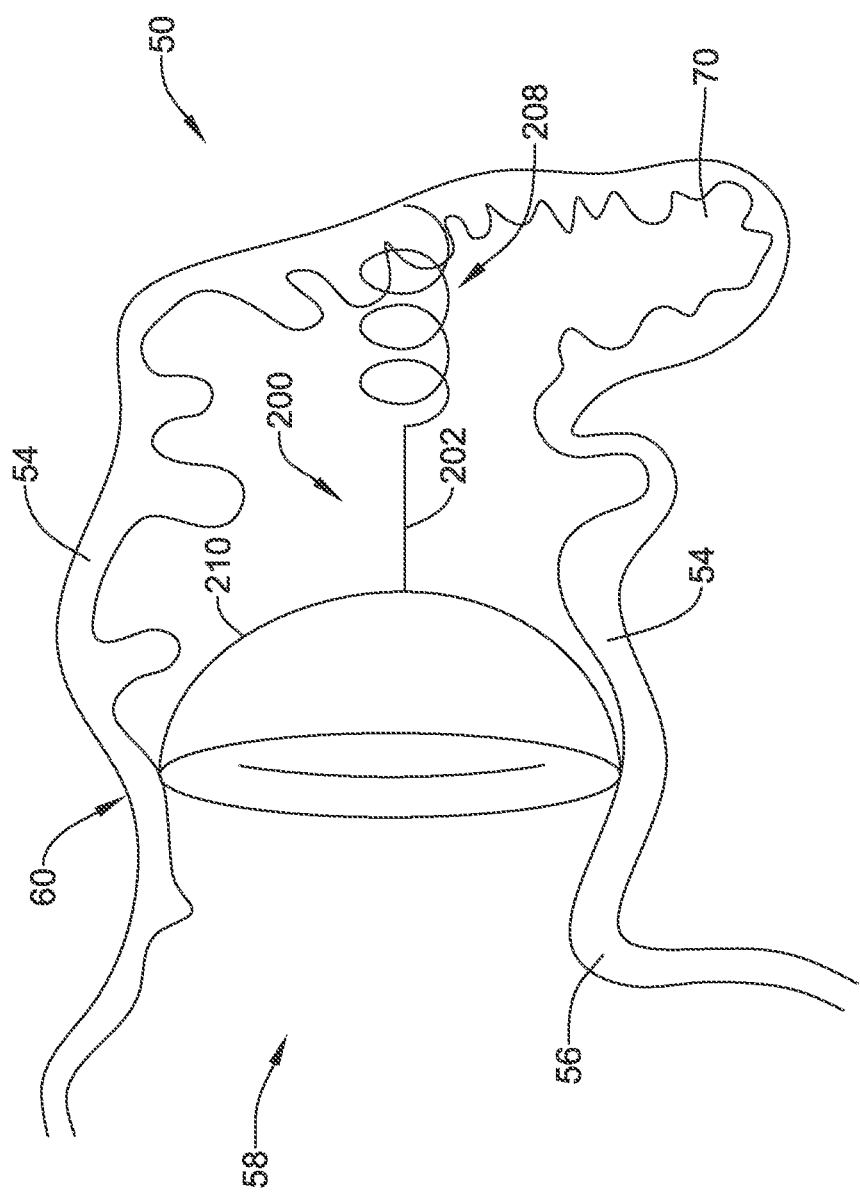
FIG. 9 is a partial schematic view of an example medical implant disposed within the example left atrial appendage of FIG. 2.

In some embodiments, the cup-shaped occluder 210 may be configured to expand radially outward from a delivery configuration to a deployed configuration. In some embodiments, the cup-shaped occluder 210 may be arranged and/or disposed generally along and immediately adjacent to the central elongate shaft 202 in the delivery configuration. In some embodiments, the cup-shaped occluder 210 may be arranged and/or disposed extending radially outward and proximally from the central elongate shaft 202 in the deployed configuration. In some embodiments, the cup-shaped occluder 210 may be concave in a proximal direction when in the deployed configuration, as seen in FIGS. 8 and 9 for example. In some embodiments, the cup-shaped occluder 210 may extend away from the central elongate shaft 202 along a curve or a curvilinear arc. In some embodiments, the cup-shaped occluder 210 may be self-biased toward the deployed configuration.

In some embodiments, the medical implant 200 may include a central elongate shaft 202 having an anchor 208 disposed at, fixed to, and/or fixedly attached at a distal end thereof. In some embodiments, the anchor 208 may extend distally from the distal end of the central elongate shaft 202. As shown in FIG. 9, in at least some embodiments, the anchor 208 may be configured to penetrate a wall 54 of a left atrial appendage 50. In some embodiments, the anchor 208 may be generally helical in shape or orientation, a helical structure including an inclined plane rotating continuously about a central axis of the anchor 208 (e.g., a screw or screw-like structure), and/or a helical coil. In at least some embodiments, the anchor 208 may include a plurality of turns. In some embodiments, the anchor 208 may be formed from a polymeric or metallic material.

In some embodiments, the anchor 208 may include one or more barbs extending radially outward from the central elongate shaft 202, similar to the medical implant 100 of FIG. 4. In some embodiments, the one or more barbs may be rigid and/or fixed in position relative to the central elongate shaft 202. In some embodiments, each of the one or more barbs may extend proximally from the central elongate shaft 202 to a free end. In some embodiments, the one or more barbs may be configured to actuate and/or shift between retracted configuration (e.g., wherein the free end of each of the one or more barbs may be positioned proximate the central elongate shaft 202) and a radially extended configuration (e.g., wherein the free end of each of the one or more barbs may be positioned radially outward from the central elongate shaft 202 and/or the retracted configuration). In some embodiments, the one or more barbs may be self-biased toward the radially extended position. In some embodiments, the one or more barbs may include two barbs, three barbs, four barbs, five barbs, or more barbs as desired. In some embodiments, the one or more barbs may be spaced equidistantly (e.g., at regular intervals or angles) about a central longitudinal axis of the central elongate shaft 202. In some embodiments, the one or more barbs may be spaced irregularly about the central longitudinal axis of the central elongate shaft 202. In some embodiments, the one or more barbs may be attached to the central elongate shaft 202 at a common axial position along the central elongate shaft 202. In some embodiments, the one or more barbs may be positioned at a plurality of axial positions along the central elongate shaft 202.

In use, the medical implant 200 may initially be disposed within a lumen of a delivery sheath in the delivery configuration, with the anchor 208 oriented distally, as in the example described above with respect to the medical implant 100. The medical implant 200 may be delivered and/or deployed in a manner similar to that described above with respect to the medical implant 100. In at least some embodiments, a deployment shaft may be disposed within the lumen of the delivery sheath proximal of the medical implant 200. In some embodiments, the deployment shaft may be releasably coupled to a proximal end of the central elongate shaft 202 of the medical implant 200. In some embodiments, rotation of the deployment shaft in a first direction (e.g., clockwise) may cause the central elongate shaft 202 and the anchor 208 fixed thereto to rotate in the first direction.

The delivery sheath and the medical implant 200, in the delivery configuration, may be advanced and/or navigated to a left atrial appendage 50 or other suitable target site. In some embodiments, a distal end of the delivery sheath may be advanced to the ostium 56 of the left atrial appendage 50, but remain outside of the left atrial appendage 50 itself. In some embodiments, a distal end of the delivery sheath may be inserted past the ostium 56 of the left atrial appendage 50 and into the left atrial appendage 50. The deployment shaft may be advanced distally within and/or relative to the delivery sheath to advance and/or translate the anchor 208 out the distal end of the delivery sheath. In some embodiments, the deployment shaft may be held stationary and the delivery sheath may be retracted proximally relative to the deployment shaft to advance and/or translate the anchor 208 out the distal end of the delivery sheath. After the anchor 208 is exposed at the distal end of the delivery sheath, the deployment shaft may be advanced and/or rotated to insert the anchor 208 into the wall 54 of the left atrial appendage 50. In some embodiments, the anchor 208 may be inserted into the wall 54 while the cup-shaped occluder 210 remains within the delivery sheath. In some embodiments, the cup-shaped occluder 210 may be deployed from the delivery sheath and/or disposed within the left atrial appendage 50 before or while the deployment shaft rotates the central elongate shaft 202 and/or the anchor 208.

A depth of deployment of the medical implant 200 within the left atrial appendage 50 may be changed or modified. For example, insertion depth of the anchor 208 into the wall 54 of the left atrial appendage 50 may affect depth of deployment of the medical implant 200, as a deeper insertion depth of the anchor 208 may result in a deeper depth of deployment of the cup-shaped occluder 210 and/or the medical implant 200. For example, in some embodiments, addition turns of rotation of the anchor 208 may bring the central elongate shaft 202 closer to the wall 54 of the left atrial appendage and the medical implant 200 deeper into the left atrial appendage 50 overall.

After the anchor 208 has been inserted into the wall 54 of the left atrial appendage 50, the delivery sheath may be withdrawn proximally and removed from the patient, leaving the medical implant 200 disposed within the left atrial appendage 50, as seen in FIG. 9, for example.

Following deployment of the medical implant 200, a portion of the left atrial appendage 50 may be blocked off and/or removed from the circulatory system, reducing or eliminating the stagnant pooling of blood, and/or reducing or avoiding the formation of thrombi, thereby lowering the risk of stroke due to thrombolytic material entering the blood stream from the left atrial appendage 50. Generally speaking, any thrombi which form within the left atrial appendage 50 behind the medical implant 200 remain trapped within the left atrial appendage 50. In some embodiments, the medical implant 200 may reduce the volume of an interior of the left atrial appendage 50 by at least 25%, by at least 40%, by at least 50%, by at least 65%, by at least 75%, by at least 90%, or other suitable amounts as desired. In some embodiments, only a portion of the left atrial appendage 50 may be blocked off and/or removed from the circulatory system. Accordingly, at least a portion of the left atrial appendage 50 may still serve useful functions and/or purposes, such as those described herein. In some embodiments, the medical implant 200 may act to lyse emboli that form within the left atrial appendage 50 distal of the medical implant 200, thereby reducing the size of the emboli to a safer level which may prevent the thrombi from causing blood vessel blockage and/or stroke.

Figure 10:
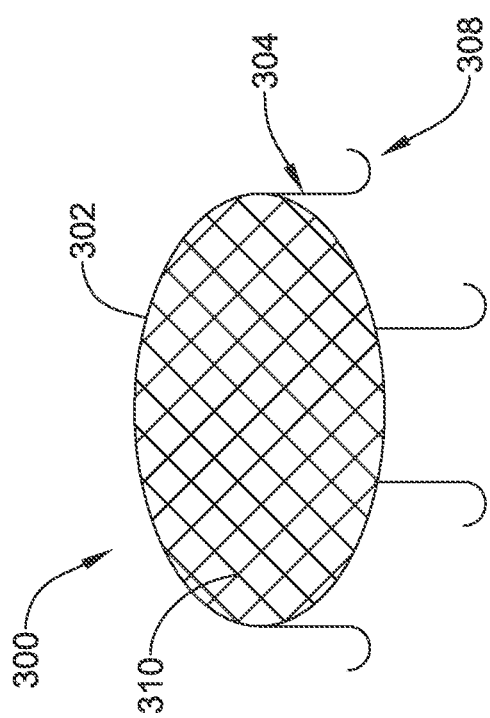
FIG. 10 is a schematic view of an example medical implant.

FIG. 10 generally illustrates an example medical implant 300 of a medical implant system for use in a left atrial appendage (50, FIG. 2), the medical implant 300 having an expandable frame 302 including a plurality of legs 304 each having an anchor 308 at a distal end thereof, and a mesh 310 attached to the expandable frame 302, the mesh having a plurality of openings therethrough. In some embodiments, the expandable frame 302 may be configured to expand radially outward from a collapsed delivery configuration (e.g., with the plurality of legs 304 oriented distally and the expandable frame 302 and the plurality of legs 304 collapsed radially inward) to a deployed configuration (e.g., with the expandable frame 302 expanded outward). In some embodiments, the expandable frame 302 may be biased outward in the deployed configuration and/or when unconstrained, for example by the elongate delivery sheath 350. In some embodiments, the expandable frame 302 may be self-biased toward the deployed configuration. In some embodiments, the plurality of legs 304 may be arranged and/or disposed extending distally from the expandable frame 302 to the anchor 308 in the deployed configuration.

In some embodiments, the anchor(s) 308 may be fixed to and/or fixedly attached at the distal end of each of the plurality of legs 304. In some embodiments, each of the plurality of legs 304 may extend distally from the expandable frame 302 to the anchor 308. In some embodiments, the anchor(s) 308 may be formed from a polymeric or metallic material. In some embodiments, the anchor(s) 308 may be configured to grab and/or penetrate into a wall (54, FIG. 2) of the left atrial appendage. In some embodiments, the plurality of legs 304 may be spaced equidistantly (e.g., at regular intervals or angles) about the expandable frame 302. In some embodiments, the plurality of legs 304 may be spaced irregularly about the expandable frame 302. In some embodiments, the plurality of legs 304 may be attached to the expandable frame 302 at a common axial position along the expandable frame 302. In some embodiments, the plurality of legs 304 may be positioned at a plurality of axial positions along the expandable frame 302.

In some embodiments, the anchor(s) 308 may include one or more barbs extending radially outward from the plurality of legs 304. In some embodiments, the one or more barbs may be rigid and/or fixed in position relative to the plurality of legs 304. In some embodiments, each of the one or more barbs may extend proximally from a distal curve or bend to a proximal free end. In some embodiments, the one or more barbs may be configured to actuate and/or shift between a retracted configuration (e.g., wherein the proximal free end of each of the one or more barbs may be positioned proximate the plurality of legs 304) and a radially extended configuration (e.g., wherein the proximal free end of each of the one or more barbs may be positioned radially outward from the plurality of legs 304 and/or the retracted configuration). In some embodiments, the one or more barbs may be self-biased toward the radially extended position. In some embodiments, the one or more barbs may include two barbs, three barbs, four barbs, five barbs, or more barbs as desired. In some embodiments, the one or more barbs may be spaced equidistantly (e.g., at regular intervals or angles) about the plurality of legs 304. In some embodiments, the one or more barbs may be spaced irregularly about the plurality of legs 304. In some embodiments, the one or more barbs may be attached to the plurality of legs 304 at a common axial position along the plurality of legs 304. In some embodiments, the one or more barbs may be positioned at a plurality of axial positions along the plurality of legs 304.

Figure 11:
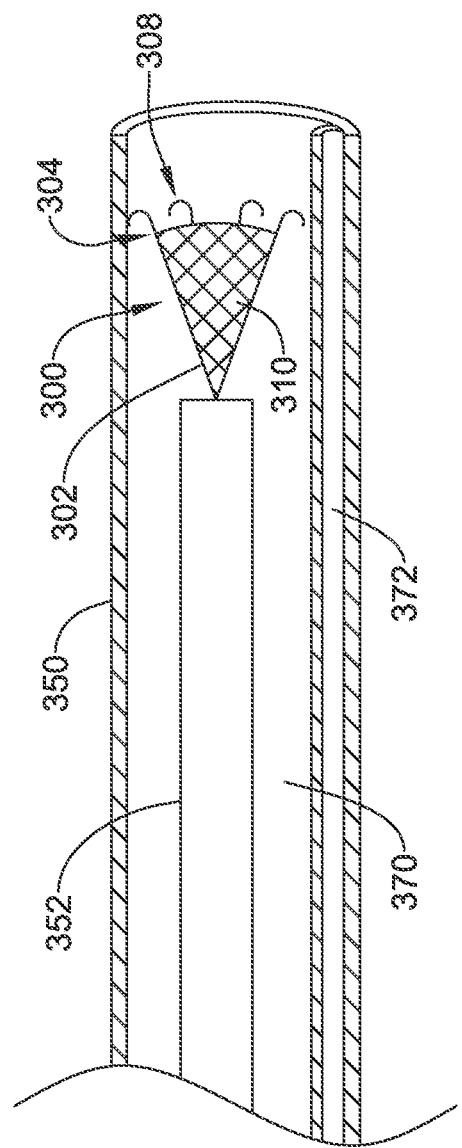
FIG. 11 is a partial schematic view of an example medical implant system.
Figure 12:
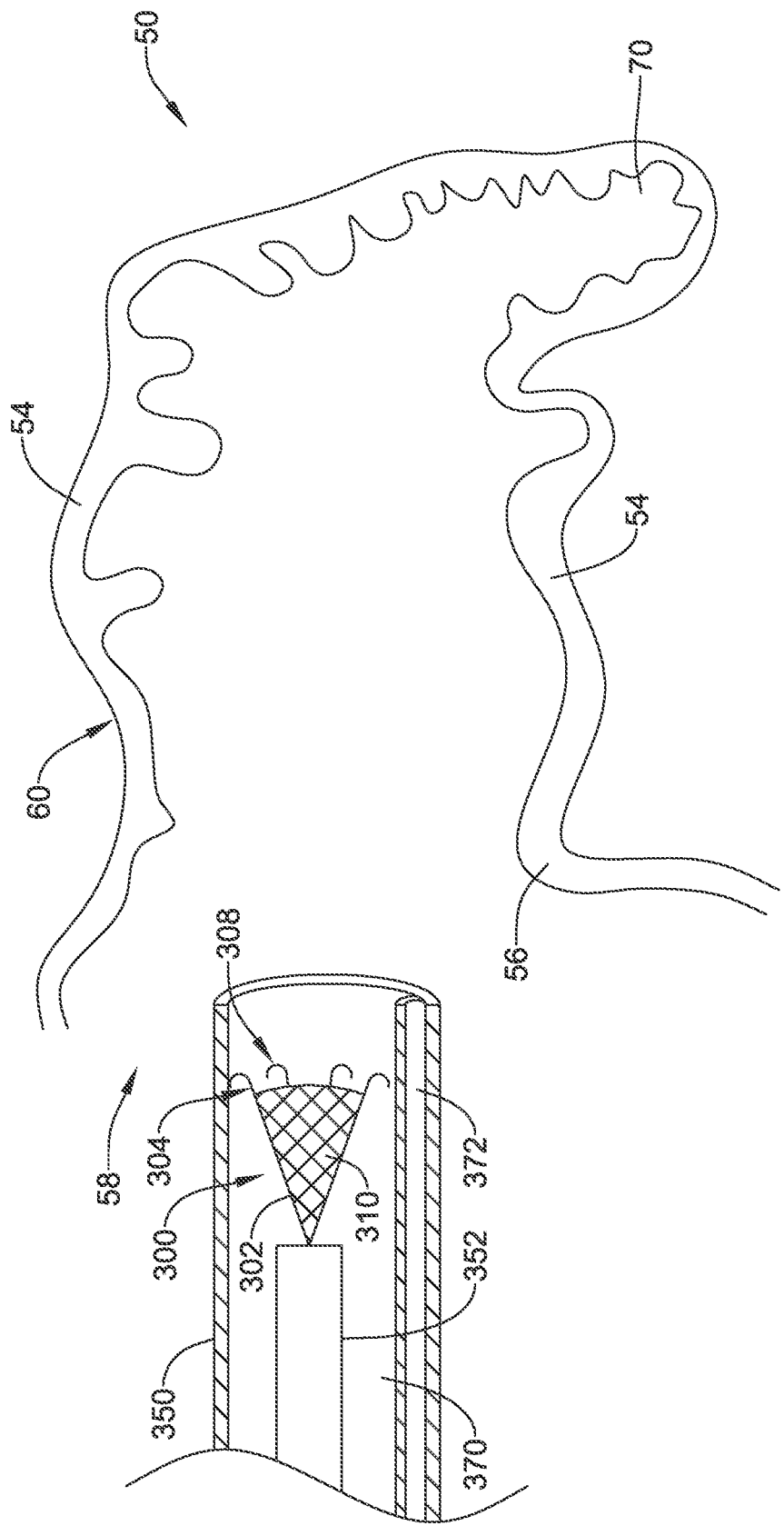
FIGS. 12-14 illustrate deployment of an example medical implant in the example left atrial appendage of FIG. 2.

As shown in FIGS. 11 and 12, in some embodiments, the medical implant system may include the medical implant 300 disposed within an elongate delivery sheath 350 having at least one lumen extending therethrough. In some embodiments, the expandable frame 302 may be arranged and/or disposed in the collapsed delivery configuration within the elongate delivery sheath 350. In some embodiments, the mesh 310 may be disposed on, over, and/or within the expandable frame 302. In some embodiments, the plurality of legs 304 may be arranged and/or disposed extending distally from the expandable frame 302 to the anchor 308 in the delivery configuration. In some embodiments, when the expandable frame 302 is in the collapsed delivery configuration, the medical implant 300 may be disposed within and deployable from the elongate delivery sheath 350, for example, in a first lumen 370 of the at least one lumen.

Figure 13:
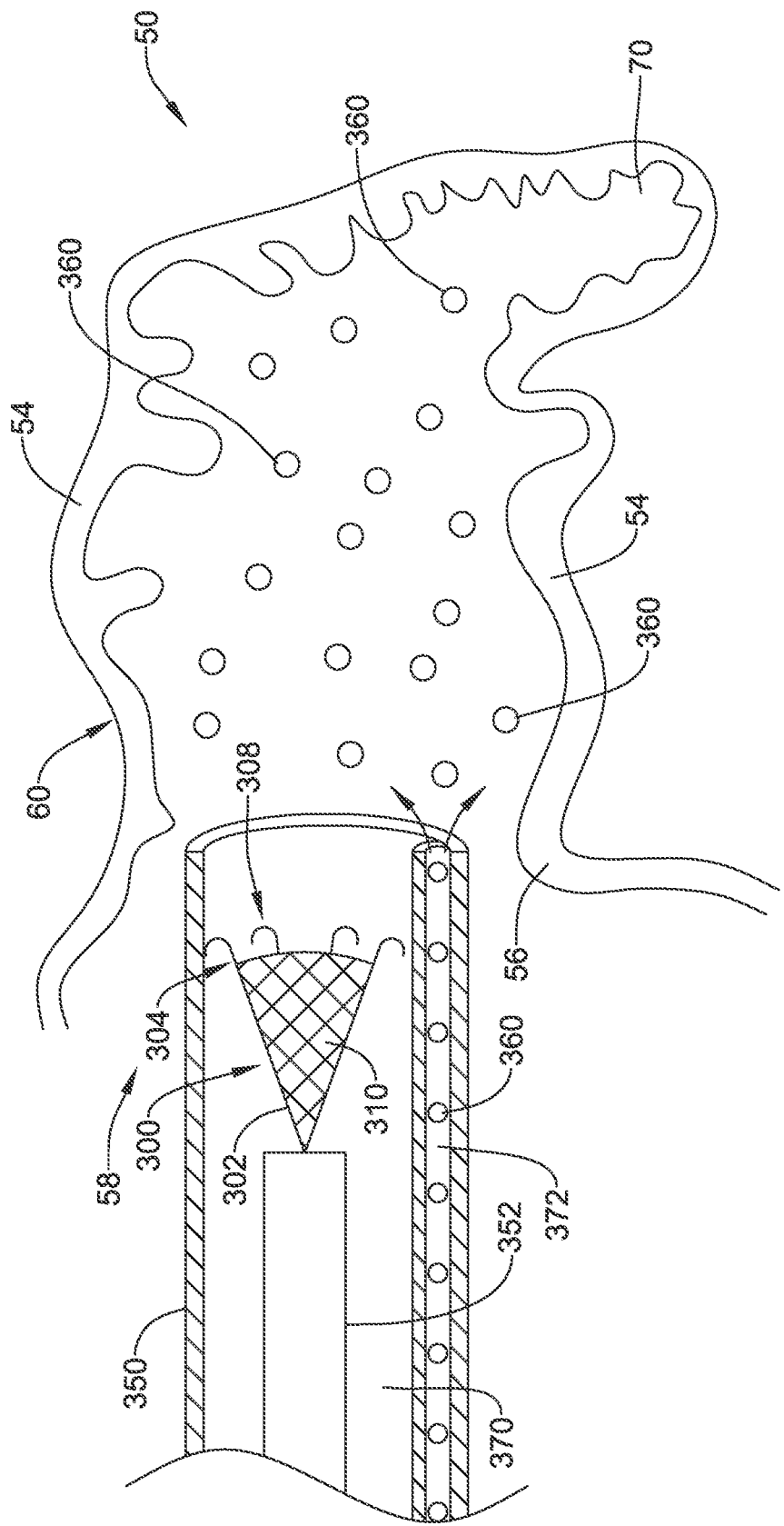

As seen in FIG. 13, in some embodiments, the medical implant system may further include a plurality of biocompatible, non-biodegradable particles 360 disposed within and deployable from the elongate delivery sheath 350, for example, in a second lumen 372 of the at least one lumen. In some embodiments, the plurality of biocompatible, non-biodegradable particles 360 and the medical implant 300 may be disposed within and deployable from the elongate delivery sheath 350 from a common lumen (i.e., the same lumen) of the at least one lumen. In some embodiments, each of the plurality of biocompatible, non-biodegradable particles 360 may be greater in size than all of the plurality of openings in the mesh 310. In some embodiments, the elongate delivery sheath 350 may be configured to release the plurality of biocompatible, non-biodegradable particles 360 distally of the medical implant 300. In some embodiments, the plurality of biocompatible, non-biodegradable particles 360 may be disposed within and/or deployable from a separate delivery device alongside or in conjunction with the medical implant system. In some embodiments, the plurality of biocompatible, non-biodegradable particles 360 may be configured to expand after delivery and/or deployment within the left atrial appendage 50, such as by absorbing a fluid (e.g., water, blood, etc.) or some other suitable means, to a size greater than all of the plurality of openings in the mesh 310.

Figure 14:
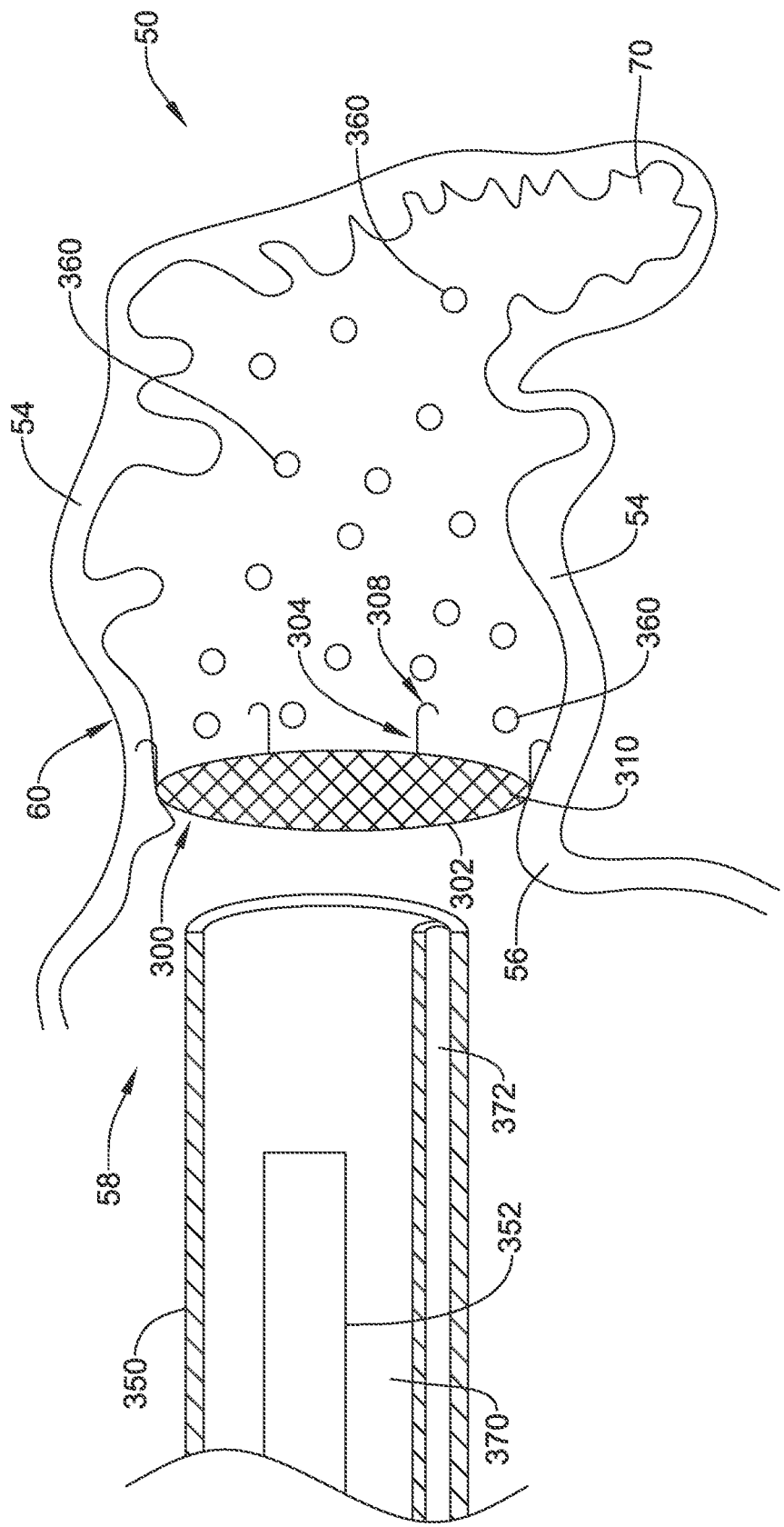

In some embodiments, the mesh 310 may be configured to retard tissue ingrowth thereon. In some embodiments, the mesh 310 may include an anti-thrombogenic surface, an anti-thrombogenic coating disposed thereon, an anti-thrombogenic agent embedded therein, and/or be made or formed from a non-thrombogenic composition. In some embodiments, the plurality of openings through the mesh 310 may be sized and configured to prevent emboli from passing therethrough while permitting blood to flow freely therethrough. In some embodiments, after deployment of the medical implant 300 in the left atrial appendage 50 and release of the plurality of biocompatible, non-biodegradable particles 360 distally of the medical implant 300, as seen in FIG. 14 for example, the plurality of biocompatible, non-biodegradable particles 360 is retained within the left atrial appendage 50 by the mesh 310 and the plurality of biocompatible, non-biodegradable particles 360 is free-floating and configured to randomly move within the left atrial appendage 50 to lyse emboli that form therein. In some embodiments, after release of the medical implant 300, at least a portion of the left atrial appendage 50 may still serve useful functions and/or purposes, such as those described herein. In some embodiments, the medical implant 300 (e.g., the mesh 310 and/or the plurality of biocompatible, non-biodegradable particles 360) may act to lyse emboli that form within the left atrial appendage 50 distal of the medical implant 300, thereby reducing the size of the emboli to a safer level which may prevent the thrombi from causing blood vessel blockage and/or stroke.

In use, the medical implant 300 may be disposed within one of at least one lumen (for example, a first lumen 370) of a elongate delivery sheath 350 in the delivery configuration, with the plurality of legs 304 and/or the anchor(s) 308 oriented distally, as seen in FIGS. 11, 12, and 13 for example. In at least some embodiments, a deployment shaft 352 may be disposed within the one of at least one lumen (e.g., the first lumen 370) of the elongate delivery sheath 350 proximal of the medical implant 300. In some embodiments, the deployment shaft 352 may be releasably coupled to a proximal portion of the medical implant 300.

The elongate delivery sheath 350 and the medical implant 300, in the delivery configuration, may be advanced and/or navigated to a left atrial appendage 50 or other suitable target site. In some embodiments, a distal end of the elongate delivery sheath 350 may be advanced to the ostium 56 of the left atrial appendage 50, as seen in FIG. 12 for example, and a distal end of the elongate delivery sheath 350 may be inserted into and/or past the ostium 56 of the left atrial appendage 50 and into the left atrial appendage 50, as seen in FIG. 13 for example. In some embodiments, a plurality of biocompatible, non-biodegradable particles 360 may be released from within the elongate delivery sheath 350 (from a second lumen 372 of the elongate delivery sheath 350, for example) into the left atrial appendage 50, as seen in FIG. 13. In some embodiments, the plurality of biocompatible, non-biodegradable particles 360 may be injected into the left atrial appendage 50, for example, alone or disposed in suspension with a biocompatible liquid.

In some embodiments, either before or after releasing the plurality of biocompatible, non-biodegradable particles 360, the deployment shaft 352 may be advanced distally within and/or relative to the elongate delivery sheath 350 to advance and/or translate the medical implant 300 and/or the anchor(s) 308 out the distal end of the elongate delivery sheath 350. In some embodiments, the deployment shaft 352 may be held stationary and the elongate delivery sheath 350 may be retracted proximally relative to the deployment shaft 352 to advance and/or translate the medical implant 300 and/or the anchor(s) 308 out the distal end of the elongate delivery sheath 350 within the ostium 56 of the left atrial appendage 50. After the medical implant 300 and/or the anchor(s) 308 is exposed at the distal end of the elongate delivery sheath 350, radially outward expansion of the expandable frame 302 may cause the anchor(s) 308 to engage and/or penetrate into the wall 54 of the left atrial appendage 50, with the mesh 310 spread across the ostium 56, thereby trapping and/or retaining the plurality of biocompatible, non-biodegradable particles 360 within the left atrial appendage 50, as seen in FIG. 14 for example.

In some embodiments, the medical implant 300 may be configured to permit the plurality of biocompatible, non-biodegradable particles 360 to be released and/or injected into the left atrial appendage 50 after deployment of the medical implant 300 within the ostium 56 of the left atrial appendage 50. For example, in some embodiments, the medical implant may include a port, a one-way valve, or other suitable structure that may permit the plurality of biocompatible, non-biodegradable particles 360 to be released and/or injected through or around the medical implant 300 and/or the mesh 310.

A depth of deployment of the medical implant 300 within the ostium 56 of the left atrial appendage 50 may be controlled in several ways. For example, a depth of the distal end of the elongate delivery sheath 350 within the ostium 56 may be pre-determined to position the medical implant 300 at a desired depth of deployment. In some embodiments, the medical implant 300 may be pushed distally further into the left atrial appendage 50 after its initial deployment. The anchor(s) 308 on the plurality of legs 304 may be configured to disengage from the wall 54 under a pre-determined distally-directed force, and then re-engage and/or re-penetrate the wall 54 of the left atrial appendage 50 upon removal of the distally-directed force, thereby preventing the medical implant 300 from being expelled from the left atrial appendage 50.

After the medical implant 300 has been deployed and the anchor(s) 308 engaged with and/or penetrated into the wall 54 of the left atrial appendage 50, the elongate delivery sheath 350 may be withdrawn proximally and removed from the patient, leaving the medical implant 300 disposed within the ostium 56 of the left atrial appendage 50.

In some embodiments, after deployment, implantation, and/or release (e.g., disengagement from the deployment shaft) of the medical implant(s) described herein, at least a portion of the left atrial appendage may still serve useful functions and/or purposes, such as those described herein. For example, in some embodiments, the medical implant(s) may act to lyse emboli that form within the left atrial appendage distal of the medical implant(s), thereby reducing the size of the emboli to a safer level which may prevent the thrombi from causing blood vessel blockage and/or stroke.

As shown in FIG. 15, the deployment shaft 152 may include a threaded engagement member 151 configured to threadably engage with the attachment member 154, for example. In some embodiments, a release wire 156 may slidably engage with both the threaded engagement member 151 of the deployment shaft 152 and the attachment member 154 to lock the deployment shaft 152 and the attachment member 154 together (e.g., to prevent relative rotational motion between the threaded engagement member 151 of the deployment shaft 152 and the attachment member 154 so as to prevent being detached or disengaged from each other). In some embodiments, the threaded engagement member 151 of the deployment shaft 152 and the attachment member 154 may each include an axially-oriented slot configured to slidably receive the release wire 156 therein. In some embodiments, the release wire 156 may extend axially alongside the deployment shaft 152 through a lumen of the delivery sheath (150, FIG. 5). In some embodiments, the release wire 156 may extend axially through a lumen of the deployment shaft 152.

When the release wire 156 is engaged with the threaded engagement member 151 of the deployment shaft 152 and the attachment member 154, rotation of the deployment shaft 152 in the first direction (e.g., clockwise) may transmit the rotation and/or torque through the threaded engagement member 151 to the attachment member 154, the central elongated member 102, and/or the anchor (108, FIG. 5)—and in at least some embodiments, may drive the anchor into the wall (54, FIG. 2) of the left atrial appendage (50, FIG. 2). When the release wire 156 is engaged with the threaded engagement member 151 of the deployment shaft 152 and the attachment member 154, rotation of the deployment shaft 152 in a second direction, opposite the first direction (e.g., counterclockwise), may transmit the rotation and/or torque through the threaded engagement member 151 to the attachment member 154, the central elongated member 102, and/or the anchor—and may withdraw the anchor from the wall of the left atrial appendage.

After the release wire 156 has been withdrawn from and/or disengaged from the threaded engagement member 151 of the deployment shaft 152 and the attachment member 154, rotation of the deployment shaft 152 in the first direction (e.g., clockwise) may transmit the rotation and/or torque through the threaded engagement member 151 to the attachment member 154, the central elongated member 102, and/or the anchor—and in at least some embodiments, may drive the anchor into the wall of the left atrial appendage. In some embodiments, after the release wire 156 has been withdrawn from and/or disengaged from the threaded engagement member 151 of the deployment shaft 152 and the attachment member 154, the deployment shaft 152

(and/or the threaded engagement member 151) may be rotated in the second direction, opposite the first direction (e.g., counterclockwise), to disengage from and/or detach from the central elongated member 102. In other words, after withdrawal and/or disengagement of the release wire 156 from the threaded engagement member 151 of the deployment shaft 152 and the attachment member 154, rotation of the deployment shaft 152 in the second direction (e.g., counterclockwise) separates and/or disengages the threaded engagement member 151 of the deployment shaft 152 from the attachment member 154, thereby releasing the medical implant 100. In general, a torque value required to disengage the threaded engagement member 151 of the deployment shaft 152 from the attachment member 154 (after the release wire 156 has been withdrawn and/or disengaged therefrom, or without the release wire 156 in place) may be less than a torque value required to extract, withdraw, and/or remove the anchor from the wall of the left atrial appendage.

As shown in FIG. 16, for example, the deployment shaft 152 may include a male connector 155 configured to matingly engage with the attachment member 154 and/or a female connector associated therewith or formed therein. In some embodiments, the male connector 155 and the female connector may have a complimentary and/or a corresponding shape (e.g., both may be square, triangular, star-shaped, polygonal, etc.) such that when engaged, relative rotation between the male connector 155 of the deployment shaft 152 and the female connector of the attachment member 154 is prevented. In some embodiments, a release wire 156 may be engaged with the male connector 155 of the deployment shaft 152 and the female connector of the attachment member 154. In some embodiments, the male connector 155 of the deployment shaft 152 may include a transverse aperture 163 configured to slidably receive the release wire 156 therein. In some embodiments, the female connector of the attachment member 154 may include a transverse aperture 161 configured to slidably receive the release wire 156 therein. In some embodiments, the transverse aperture 161 of the female connector of the attachment member 154 and the transverse aperture 163 of the male connector 155 of the deployment shaft 152 may be aligned and/or coaxial with each other so as to slidably receive the release wire 156 therein, as seen in FIG. 16 for example. When the release wire 156 is engaged with the transverse aperture 163 of the male connector 155 of the deployment shaft 152 and the transverse aperture 161 of the female connector of the attachment member 154, the male connector 155 of the deployment shaft 152 and the female connector of the attachment member 154 may be locked together and/or prevented from disengaging or separating.

When the release wire 156 is engaged with the transverse aperture 163 of the male connector 155 of the deployment shaft 152 and the transverse aperture 161 of the female connector of the attachment member 154, rotation of the deployment shaft 152 in the first direction (e.g., clockwise) may transmit the rotation and/or torque through the male connector 155 of the deployment shaft 152 to the female connector of the attachment member 154, the central elongated member 102, and/or the anchor (108, FIG. 5)—and in at least some embodiments, may drive the anchor into the wall (54, FIG. 2) of the left atrial appendage (50, FIG. 2). When the release wire 156 is engaged with the transverse aperture 163 of the male connector 155 of the deployment shaft 152 and the transverse aperture 161 of the female connector of the attachment member 154, rotation of the deployment shaft 152 in a second direction, opposite the first direction (e.g., counterclockwise), may transmit the rotation and/or torque through the male connector 155 of the deployment shaft 152 to the female connector of the attachment member 154, the central elongated member 102, and/or the anchor—and may withdraw the anchor from the wall of the left atrial appendage.

After the release wire 156 has been withdrawn from and/or disengaged from the transverse aperture 163 of the male connector 155 of the deployment shaft 152 and the transverse aperture 161 of the female connector of the attachment member 154, rotation of the deployment shaft 152 in the first direction (e.g., clockwise) may transmit the rotation and/or torque through the male connector 155 of the deployment shaft 152 to the female connector of the attachment member 154, the central elongated member 102, and/or the anchor—and in at least some embodiments, may drive the anchor into the wall of the left atrial appendage—as long as the male connector 155 and/or the deployment shaft 152 has not been withdrawn proximally from the female connector and/or the attachment member 154. In some embodiments, after the release wire 156 has been withdrawn from and/or disengaged from the transverse aperture 163 of the male connector 155 of the deployment shaft 152 and the transverse aperture 161 of the female connector of the attachment member 154, rotation of the deployment shaft 152 in a second direction, opposite the first direction (e.g., counterclockwise), may transmit the rotation and/or torque through the male connector 155 of the deployment shaft 152 to the female connector of the attachment member 154, the central elongated member 102, and/or the anchor 108—and may withdraw the anchor from the wall of the left atrial appendage—as long as the male connector 155 and/or the deployment shaft 152 has not been withdrawn proximally from the female connector and/or the attachment member 154. In other words, after withdrawal and/or disengagement of the release wire 156 from the transverse aperture 163 of the male connector 155 of the deployment shaft 152 and the transverse aperture 161 of the female connector of the attachment member 154, withdrawal of the male connector 155 and/or the deployment shaft 152 separates the male connector 155 of the deployment shaft 152 from the female connector of the attachment member 154, thereby releasing the medical implant 100.

Figure 17:
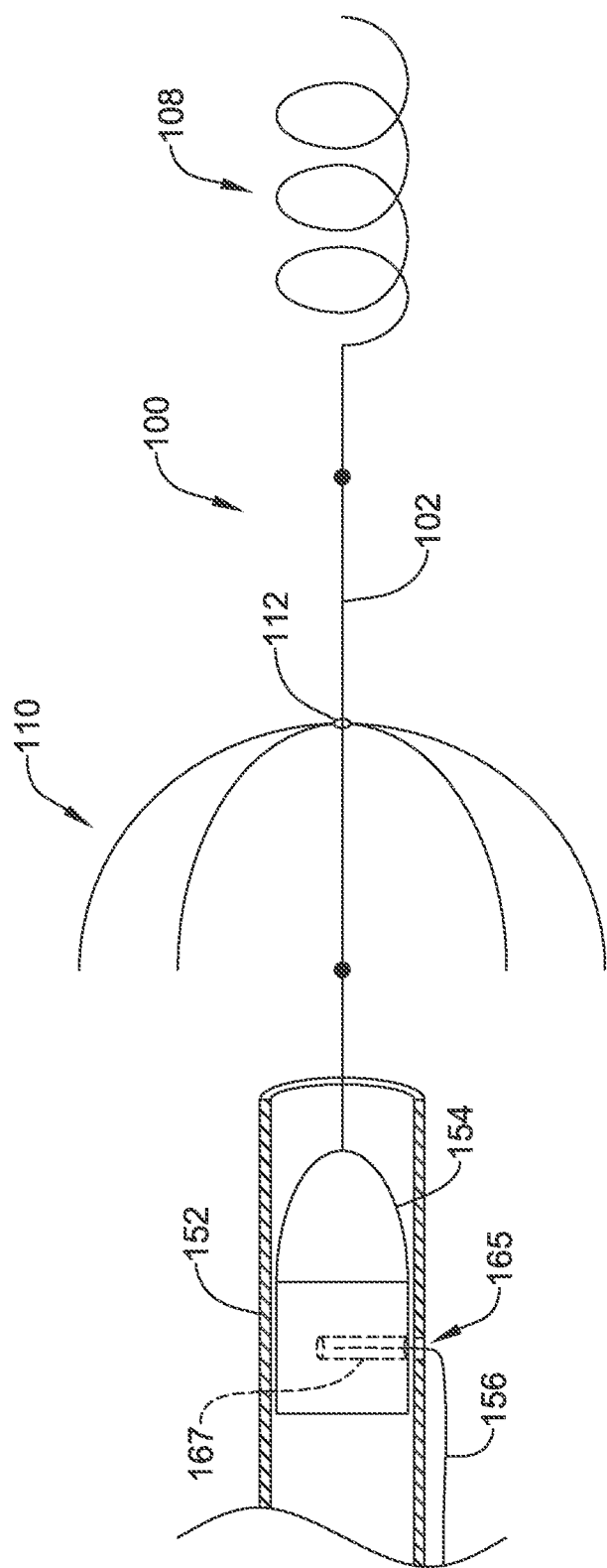
FIG. 17 illustrates an example attachment member for an example medical implant.

As shown in FIG. 17, in some embodiments, the deployment shaft 152 may include and/or form a female connector configured to matingly engage with the attachment member 154 and/or a male connector associated therewith or formed thereby. In some embodiments, the male connector and the female connector may have a complimentary and/or a corresponding shape (e.g., both may be square, triangular, star-shaped, polygonal, etc.) such that when engaged, relative rotation between the female connector of the deployment shaft 152 and the male connector of the attachment member 154 is prevented. In some embodiments, a release wire 156 may be engaged with the female connector of the deployment shaft 152 and the male connector of the attachment member 154. In some embodiments, the female connector of the deployment shaft 152 may include a transverse aperture 165 configured to slidably receive the release wire 156 therein. In some embodiments, the male connector of the attachment member 154 may include a transverse aperture 167 configured to slidably receive the release wire 156 therein. When the release wire 156 is engaged with the transverse aperture 165 of the female connector of the deployment shaft 152 and the transverse aperture 167 of the male connector of the attachment member 154, the female connector of the deployment shaft 152 and the male connector of the attachment member 154 may be locked together and/or prevented from disengaging or separating.

When the release wire 156 is engaged with the transverse aperture 165 of the female connector of the deployment shaft 152 and the transverse aperture 167 of the male connector of the attachment member 154, rotation of the deployment shaft 152 in the first direction (e.g., clockwise) may transmit the rotation and/or torque through the female connector of the deployment shaft 152 to the male connector of the attachment member 154, the central elongated member 102, and/or the anchor 108—and in at least some embodiments, may drive the anchor 108 into the wall (54, FIG. 2) of the left atrial appendage (50, FIG. 2). When the release wire 156 is engaged with the transverse aperture 165 of the female connector of the deployment shaft 152 and the transverse aperture 167 of the male connector of the attachment member 154, rotation of the deployment shaft 152 in a second direction, opposite the first direction (e.g., counterclockwise), may transmit the rotation and/or torque through the female connector of the deployment shaft 152 to the male connector of the attachment member 154, the central elongated member 102, and/or the anchor 108—and may withdraw the anchor 108 from the wall of the left atrial appendage.

After the release wire 156 has been withdrawn from and/or disengaged from the transverse aperture 165 of the female connector of the deployment shaft 152 and the transverse aperture 167 of the male connector of the attachment member 154, rotation of the deployment shaft 152 in the first direction (e.g., clockwise) may transmit the rotation and/or torque through the female connector of the deployment shaft 152 to the male connector of the attachment member 154, the central elongated member 102, and/or the anchor 108—and in at least some embodiments, may drive the anchor 108 into the wall of the left atrial appendage—as long as the female connector and/or the deployment shaft 152 has not been withdrawn proximally from the male connector and/or the attachment member 154. In some embodiments, after the release wire 156 has been withdrawn from and/or disengaged from the transverse aperture 165 of the female connector of the deployment shaft 152 and the transverse aperture 167 of the male connector of the attachment member 154, rotation of the deployment shaft 152 in a second direction, opposite the first direction (e.g., counterclockwise), may transmit the rotation and/or torque through the female connector of the deployment shaft 152 to the male connector of the attachment member 154, the central elongated member 102, and/or the anchor 108—and may withdraw the anchor 108 from the wall of the left atrial appendage—as long as the female connector and/or the deployment shaft 152 has not been withdrawn proximally from the male connector and/or the attachment member 154. In other words, after withdrawal and/or disengagement of the release wire 156 from the transverse aperture 165 of the female connector of the deployment shaft 152 and the transverse aperture 167 of the male connector of the attachment member 154, withdrawal of the female connector and/or the deployment shaft 152 separates the female connector of the deployment shaft 152 from the male connector of the attachment member 154, thereby releasing the medical implant 100.

Figure 18:
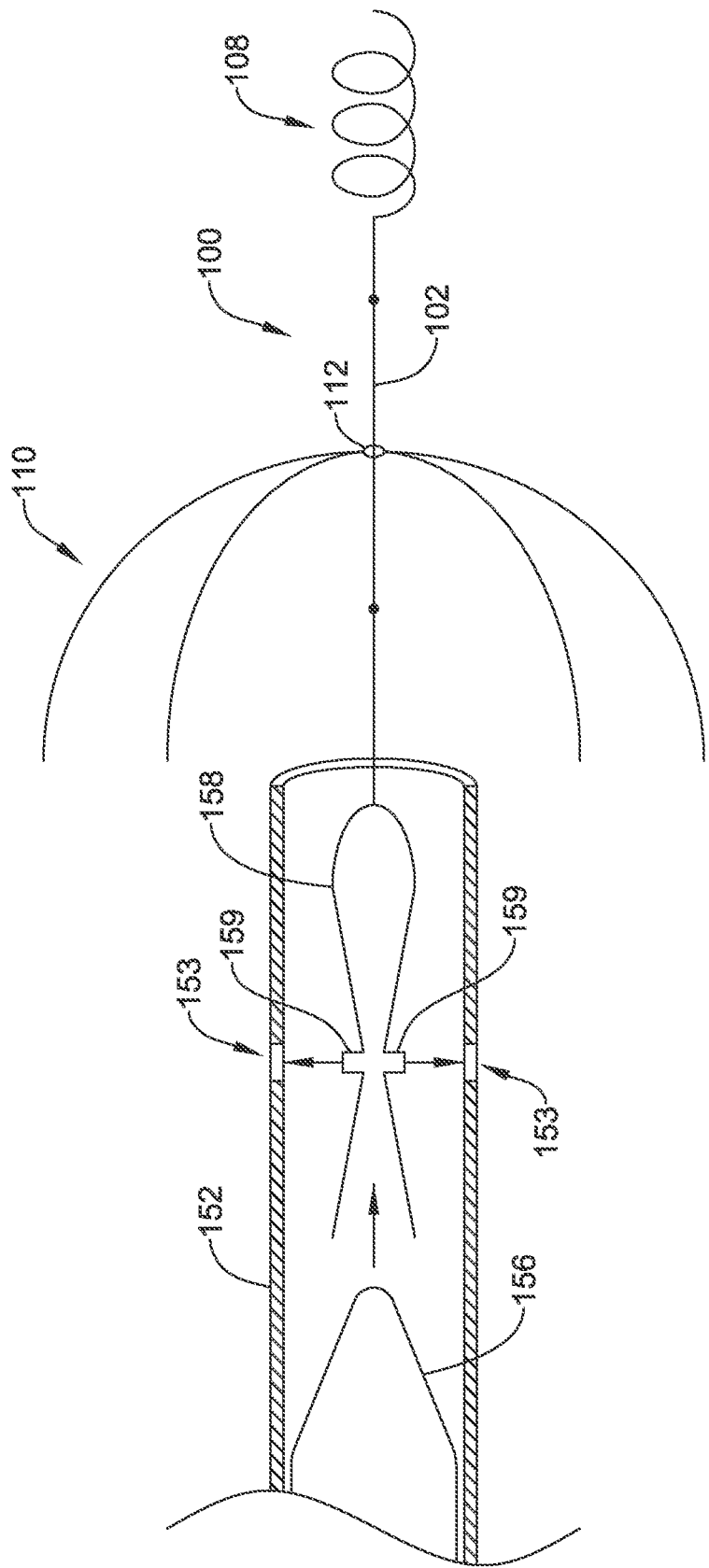
FIG. 18 is a partial section view of an example attachment member for an example medical implant.

As shown in FIG. 18, in some embodiments, the deployment shaft 152 may include one or more openings 153 configured to matingly engage with one or more corresponding engagement pins 159 on an attachment member 158 attached to and/or formed as a part of the medical implant 100, for example. In some embodiments, the deployment shaft 152 and the attachment member 158 may have a complimentary and/or a corresponding shape (e.g., both may be square, triangular, star-shaped, polygonal, etc.) such that when engaged and/or when the one or more engagement pins 159 is engaged with the one or more openings 153, relative rotation between the deployment shaft 152 and the attachment member 158 is prevented. In some embodiments, a release wire 156 may be slidably disposed within the deployment shaft 152 and/or slidably engaged with the attachment member 158 disposed within a distal end of the deployment shaft 152, thereby urging and/or forcing the one or more engagement pins 159 of the attachment member 158 outward into engagement with the one or more openings 153 of the deployment shaft 152. In some embodiments, the release wire 156 may include a rod having a tapered distal end configured to engage the attachment member 158. When the release wire 156 is engaged with the attachment member 158, the one or more engagement pins 159 of the attachment member 158 and the one or more openings 153 of the deployment shaft 152 may be locked together and/or prevented from disengaging or separating.

When the release wire 156 is engaged with the attachment member 158, rotation of the deployment shaft 152 in the first direction (e.g., clockwise) may transmit the rotation and/or torque through the attachment member 158, the central elongated member 102, and/or the anchor 108—and in at least some embodiments, may drive the anchor 108 into the wall (54, FIG. 2) of the left atrial appendage (50, FIG. 2). When the release wire 156 is engaged with the attachment member 158, rotation of the deployment shaft 152 in the second direction, opposite the first direction (e.g., counterclockwise), may transmit the rotation and/or torque through the attachment member 158, the central elongated member 102, and/or the anchor 108—and may withdraw the anchor 108 from the wall of the left atrial appendage.

After the release wire 156 has been withdrawn from and/or disengaged from the attachment member 158, the attachment member 158 may collapse inward toward a longitudinal axis of the medical implant 100. In some embodiments, the attachment member 158 may be self-biased inwardly. In some embodiments, after the release wire 156 has been withdrawn from and/or disengaged from the attachment member 158, rotation of the deployment shaft 152 in the first direction or the second direction may fail to transmit rotation and/or torque to the attachment member 158, the central elongated member 102, and/or the anchor 108 because the one or more engagement pins 159 of the attachment member 158 no longer engage the one or more openings 153 of the deployment shaft 152. In other words, after withdrawal and/or disengagement of the release wire 156 from the attachment member 158, the deployment shaft 152 separates from the attachment member 158, thereby releasing the medical implant 100.

In some embodiments, the deployment shaft 152 may include a rack-and-pinion gear arrangement disposed within a distal end thereof, as seen in FIG. 19, for example. In some embodiments, the deployment shaft 152 may include a push rod 160 extending longitudinally therethrough. In some embodiments, a push rod 160 may be advanced distally (and/or retracted proximally) relative to the deployment shaft 152 to effect rotation of the central elongated member 102 and the anchor 108. In some embodiments, a distal end of the push rod 160 may engage with a primary gear 162, wherein axial movement of the push rod 160 may translate into rotational movement of the primary gear 162 about a central axis thereof. In some embodiments, the primary gear 162 may engage with a secondary gear 164, wherein rotational movement of the primary gear 162 may in turn cause rotational movement of the secondary gear 164 about a central longitudinal axis of the secondary gear 164 and/or the deployment shaft 152. In some embodiments, the secondary gear 164 may be attached to and/or fixed at a proximal end of the central elongated member 102. In other words, longitudinal and/or axial translation of the push rod 160 may be converted into rotary movement and/or translation of the secondary gear 164, the central elongated member 102, and/or the anchor 108. In some embodiments, distal translation of the push rod 160 may cause rotation of the secondary gear 164, the central elongated member 102, and/or the anchor 108 in the first direction (e.g., clockwise). In some embodiments, proximal translation of the push rod 160 may cause rotation of the secondary gear 164, the central elongated member 102, and/or the anchor 108 in the second direction (e.g., counterclockwise). In some embodiments, a clutch may be provided to ensure rotation in a desired direction and/or to provide a means for selectively changing the direction of rotation. In some embodiments, the central elongated member 102 and/or the medical implant 100 may be releasably attached to the rack-and-pinion gear arrangement and/or the deployment shaft 152. In some embodiments, the central elongated member 102 may be selectively disengaged from the deployment shaft 152, the rack-and-pinion gear arrangement, and/or the secondary gear 164 to release the medical implant 100.

In some embodiments, some elements of the disclosure, such as but not limited to, the central elongated member 102, the anchor 108, the plurality of elongated metallic legs 110, the joint 112, the central elongate shaft 202, the anchor 208, the expandable frame 302, the plurality of legs 304, the anchor(s) 308, and/or the plurality of biocompatible, non-biodegradable particles 360, may be formed of or include a metallic material, a metallic alloy, a ceramic material, a rigid or high performance polymer, a metallic-polymer composite, combinations thereof, and the like. Some examples of some suitable materials may include metallic materials and/or alloys such as stainless steel (e.g., 304v stainless steel or 316L stainless steel), nickel-titanium alloy (e.g., nitinol, such as super elastic or linear elastic nitinol), nickel-chromium alloy, nickel-chromium-iron alloy, cobalt alloy, nickel, titanium, platinum, or alternatively, a polymer material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some embodiments, some elements of the disclosure, such as but not limited to the central elongated member 102, the anchor 108, the plurality of elongated metallic legs 110, the joint 112, the central elongate shaft 202, the anchor 208, the expandable frame 302, the plurality of legs 304, the anchor(s) 308, and/or the plurality of biocompatible, non-biodegradable particles 360, may be mixed with, may be doped with, may be coated with, or may otherwise include a radiopaque material. Radiopaque materials are understood to be materials capable of producing a relatively bright image on a fluoroscopy screen or another imaging technique such as X-ray during a medical procedure. This relatively bright image aids the user of device in determining its location. Suitable radiopaque materials may include, but are not limited to, bismuth subcarbonate, iodine, gold, platinum, palladium, tantalum, tungsten or tungsten alloy, and the like.

In some embodiments, some elements of the disclosure, such as but not limited to the delivery sheaths 150/250/350, the cup-shaped occluder 210, the mesh 310, and/or the anchors 108/208/308, may be formed of or include a polymeric material, a metallic or metallic alloy material, a metallic-polymer composite, combinations thereof, and the like. Examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials.

In some embodiments, the medical implants 100/200/300 and/or portions thereof, may be made from, may be mixed with, may be coated with, or may otherwise include a material that provides a smooth, slick outer surface. In some embodiments, the medical implants 100/200/300 and/or portions thereof may include or be coated with a lubricious coating, a hydrophilic coating, a hydrophobic coating, a drug-eluting material, an anti-thrombus coating, or other suitable coating depending on the intended use or application.

It should be understood that although the above discussion was focused on a medical device and methods of use within the vascular system and/or the heart of a patient, other embodiments of medical devices or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the apparatus and/or medical devices described herein with respect to percutaneous deployment may be used in other types of surgical procedures as appropriate. For example, in some embodiments, the medical devices may be deployed in a non-percutaneous procedure, such as an open heart procedure. Devices and methods in accordance with the invention can also be adapted and configured for other uses within the anatomy.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims. This may include, to the extent that it is appropriate, the use of any of the features of one example embodiment or aspect being used in other embodiments or aspects.

We claim:

1. A medical implant system for use in a left atrial appendage, comprising:
   an elongate delivery sheath having at least one lumen extending therethrough;
   an implant disposed within and deployable from the delivery sheath, the implant having an expandable frame including a plurality of legs each having an anchor at a distal end thereof, and a mesh attached to the expandable frame, the mesh having a plurality of openings therethrough; and a plurality of biocompatible, non-biodegradable particles disposed within the delivery sheath, wherein each of the plurality of biocompatible, non-biodegradable particles is greater in size than all of the plurality of openings, and wherein the plurality of biocompatible, non-biodegradable particles is retained within the left atrial appendage by the mesh and the plurality of biocompatible, non-biodegradable particles is free-floating and configured to randomly move within the left atrial appendage to lyse emboli that form therein.

2. The medical implant of claim 1, wherein the mesh is configured to retard tissue ingrowth thereon.

3. The medical implant of claim 1, wherein the plurality of openings is sized and configured to prevent emboli from passing therethrough while permitting blood flow therethrough.

4. The medical implant of claim 1, wherein delivery sheath is configured to release the plurality of particles distally of the implant.

* * * * *